(12) United States Patent
Castranova

(10) Patent No.: US 9,497,940 B2
(45) Date of Patent: Nov. 22, 2016

(54) SYSTEM AND APPARATUS FOR RESEARCH AND TESTING OF SMALL AQUATIC SPECIES

(71) Applicant: R&D Aquatics, LLC, Columbia, MD (US)

(72) Inventor: Daniel Anthony Castranova, Columbia, MD (US)

(73) Assignee: R&D AQUATICS, LLC, Columbia, MD (US)

( * ) Notice: Subject to any disclaimer, the term of this patent is extended or adjusted under 35 U.S.C. 154(b) by 0 days.

(21) Appl. No.: 14/986,138

(22) Filed: Dec. 31, 2015

(65) Prior Publication Data

US 2016/0106075 A1  Apr. 21, 2016

Related U.S. Application Data

(63) Continuation of application No. 13/765,763, filed on Feb. 13, 2013, now Pat. No. 9,226,475.

(60) Provisional application No. 61/597,901, filed on Feb. 13, 2012, provisional application No. 61/739,050, filed on Dec. 19, 2012.

(51) Int. Cl.
| | |
|---|---|
| A01K 63/00 | (2006.01) |
| A01K 1/03 | (2006.01) |
| A01K 63/04 | (2006.01) |
| A01K 67/00 | (2006.01) |
| A01K 61/00 | (2006.01) |

(52) U.S. Cl.
CPC ............ *A01K 63/003* (2013.01); *A01K 1/03* (2013.01); *A01K 1/031* (2013.01); *A01K 61/008* (2013.01); *A01K 63/04* (2013.01); *A01K 63/047* (2013.01); *A01K 67/00* (2013.01)

(58) Field of Classification Search
CPC .............................. A01K 63/00; A01K 1/03
USPC ....... 119/217, 248, 252, 417, 416, 452, 455, 119/472, 473
See application file for complete search history.

(56) References Cited

U.S. PATENT DOCUMENTS

| | | | |
|---|---|---|---|
| 3,255,731 A | 6/1966 | Girard | |
| 3,512,503 A | 5/1970 | Willinger | |
| 4,892,651 A * | 1/1990 | Hill | A01K 63/045 119/227 |
| 5,117,777 A * | 6/1992 | Takasugi | A01K 63/02 119/203 |
| 5,469,810 A * | 11/1995 | Chiang | A01K 63/003 119/225 |
| 5,551,378 A * | 9/1996 | Dewalt | A01K 63/003 119/247 |
| 6,352,051 B1* | 3/2002 | Wang | A01K 61/008 119/248 |
| 6,810,833 B2* | 11/2004 | Bonner | A01K 1/03 119/452 |
| 7,527,022 B2* | 5/2009 | Bonner | A01K 1/03 119/481 |
| 7,810,452 B2 | 10/2010 | Pieretto et al. | |
| 8,136,895 B2* | 3/2012 | Grainger | A47B 67/04 312/111 |
| 8,689,739 B2* | 4/2014 | Owens | A01K 1/03 119/417 |
| 2014/0238309 A1* | 8/2014 | Hahn | A01K 1/03 119/472 |

* cited by examiner

*Primary Examiner* — Kristen C Hayes
(74) *Attorney, Agent, or Firm* — Maldjian Law Group LLC

(57) ABSTRACT

An apparatus for testing and researching aquatic species is provided. The apparatus includes a housing rack for housing a tank. The apparatus further includes one or more dividers for dividing the at least one tank into one or more compartments. The apparatus further includes a collection channel and a downspout in each compartment for draining of water from each compartment. The apparatus further includes one or more lids for covering the one or more compartments.

19 Claims, 36 Drawing Sheets

SYSTEM AND APPARATUS FOR RESEARCH AND TESTING OF SMALL AQUATIC SPECIES

CROSS-REFERENCE TO RELATED APPLICATIONS

This application is a continuation application of U.S. application Ser. No. 13/765,763, filed Feb. 13, 2013, which claims priority to U.S. Provisional Application Ser. No. 61/597,901 filed Feb. 13, 2012, entitled "APPARATUS, SYSTEM, AND METHOD FOR RESEARCH AND TESTING OF SMALL AQUATIC SPECIES" and U.S. Provisional Application Ser. No. 61/739,050 filed Dec. 19, 2012, entitled "APPARATUS, SYSTEM, AND METHOD FOR RESEARCH AND TESTING OF SMALL AQUATIC SPECIES", all of which are incorporated herein by reference in their entirety.

BACKGROUND

Field of the Invention

Embodiments of the present invention provide an apparatus and a method for research and testing of small aquatic species, and particularly to an apparatus and method for various screening procedures of *Danio rerio*, commonly known as zebrafish.

Description of Related Art

Animals are used extensively in genetic research. Among other purposes and benefits, such genetic research helps scientists locate and understand the causes of various diseases and behaviors that manifest in humans. Many animals have enough genetic similarities to humans to make them good analogs for genetic testing, as they are easy to breed and there are lesser ethical considerations than performing genetic testing on humans. One such animal is the *Danio rerio*, commonly known as the zebrafish, which is a vertebrate like humans. Because of this similarity, it is likely that zebrafish have similar biological traits, including genes, developmental processes, anatomy, physiology, and behaviors.

Various screening processes are performed on zebrafish, such as genotyping and embryonic screening for mutant phenotypes. Currently, when DNA or embryos are being screened, the zebrafish are housed in individual tanks that range in size from about 0.8 liters to 2 liters. Such tanks are much larger than necessary. One liter can hold approximately 5-15 individual zebrafish. However, during the screening process, this volume of water is used to house either individuals or pairs of zebrafish only, which amounts to an extremely inefficient use of water and space. These tanks are commonly stored on housing racks. Because the size of each tank is so large compared to the number of zebrafish being housed in each tank, each rack is able to store only a relatively minimal amount of zebrafish. Therefore, more racks are required. This makes for a very inefficient testing set up, poor use of lab space and time consuming efforts in connection with transporting the zebrafish to and from the testing area.

In addition, due to this inefficient set up and storage method, often, the zebrafish in these tanks are kept off system where they are not adequately monitored. This may result in the water developing into poor condition, thereby becoming hazardous to the zebrafish. This may also result in unnecessary stress to the experimental animals.

Furthermore, microtiter plates are commonly used to store or house the samples/specimens extracted from the zebrafish during a screening process, particularly genotyping. A microtiter plate typically has 6, 24, 96, 384, or even 1536 sample wells arranged in a '2:3' rectangular matrix. Therefore, it is critical to the research that the tanks are properly labeled so the samples/specimens extracted from the zebrafish and stored in a specific well of a microtiter plate are matched with the appropriate zebrafish from which it was extracted. This requires an extremely painstaking and time-consuming process in which researchers, many of whom are Ph.D.'s, must use up valuable research time in order to properly label each individual tank.

Moreover, the embryonic screening process, which is very commonly performed in laboratories, involves the breeding of hundreds of pairs of zebrafish every week. After the zebrafish breed and spawn, and the embryos are collected, the spawning zebrafish are placed in holding tanks while the embryos are screened for mutant phenotypes. If the embryos show interesting phenotypes, the pair that produced those embryos is retrieved and additional steps, including out-crossing and more pair-wise crossing, are taken to isolate the gene that was mutated.

In many cases, this process could take years to isolate the mutated gene. Due to the high volume of pairs of zebrafish that are bred each week, an excessive amount of water and storage space is required. Also, given the painstaking nature and potential lengthiness of the process, it is critical that items are properly labeled and records properly kept. Again, valuable research time is wasted labeling to try to minimize the risk of errors.

Therefore, a need exists for a versatile apparatus, system, and method for various types of testing of zebrafish in an efficient and effective manner.

SUMMARY

Embodiments in accordance with the present invention provide an apparatus for testing and researching aquatic species. The apparatus includes, but is not restricted to a housing rack for housing at least one tank, one or more dividers for dividing the at least one tank into one or more compartments, a collection channel in each of the one or more compartments for draining water from the one or more compartments, one or more lids for covering the one or more compartments, at least one water supply source, one or more rails at bottom surface of the tank for locking the tank onto a tank-holding bar, at least one basket that is placed into at least one compartment of the tank for allowing easier removal of aquatic species from the tank, and a insert that may be placed into at least one tank for facilitating spawning process of the aquatic species.

Embodiments in accordance with the present invention further provide a system for testing and researching aquatic species. The system includes, but is not restricted to, at least one tank comprising compartments and sub-compartments formed by one or more dividers, a housing rack for accommodating the at least one tank, a collection channel and a downspout for each compartment for draining of water from each compartment, and one or more lids to cover each compartment, wherein the housing rack further comprises multiple shelves, drawers on shelves for resting at least one tank, drainage troughs on the shelves into which water from the downspout drain, a water collection tank into which water from the drainage troughs drain, and a pump for pumping the water from the water collection tank to water supply sources.

Embodiments in accordance with the present invention further provide a method for testing and researching small aquatic species, particularly zebrafish. The method comprises: providing a housing rack, providing at least one tank on a shelf of the housing rack, placing dividers into the at least one tank to create one or more compartments in the at least one tank, filing the at least one tank with water, and performing testing on the aquatic species.

Further, the present invention can provide a number of advantages depending on its particular configuration. First, embodiments of the present invention provide an apparatus and a method for housing small aquatic species for research purposes. Embodiments of the present invention provide a very efficient research setup by minimizing efforts and time consumption required for transportation of aquatic species from research lab. Embodiments of the present invention make a very efficient use of lab space by minimizing apparatus requirements. Embodiments of the present invention enable use of dividers to create compartments within a tank that allows a tank to accommodate more number of aquatic species. This saves a lot of space, resources, efforts, and research time.

Furthermore, by using embodiments of the present invention, the researchers will be able to save time by placing the fish in the sub-compartment. Additionally, this reduces the risk of erroneously mislabeling or mixing up of individual tanks, thereby preserving the integrity of the test results. Furthermore, valuable space in the research laboratory will be saved by housing the fish in appropriately sized sub-compartments rather than oversized tanks.

These and other advantages will be apparent from the disclosure of the present invention contained herein.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted the terms "comprising", "including", and "having" can be used interchangeably.

The preceding is a simplified summary of the present invention to provide an understanding of some aspects of the present invention. This summary is neither an extensive nor exhaustive overview of the present invention and its various embodiments. It is intended neither to identify key or critical elements of the present invention nor to delineate the scope of the present invention but to present selected concepts of the present invention in a simplified form as an introduction to the more detailed description presented below. As will be appreciated, other embodiments of the present invention are possible utilizing, alone or in combination, one or more of the features set forth above or described in detail below.

BRIEF DESCRIPTION OF THE DRAWINGS

The above and still further features and advantages of the present invention will become apparent upon consideration of the following detailed description of embodiments thereof, especially when taken in conjunction with the accompanying drawings.

Figure 1:
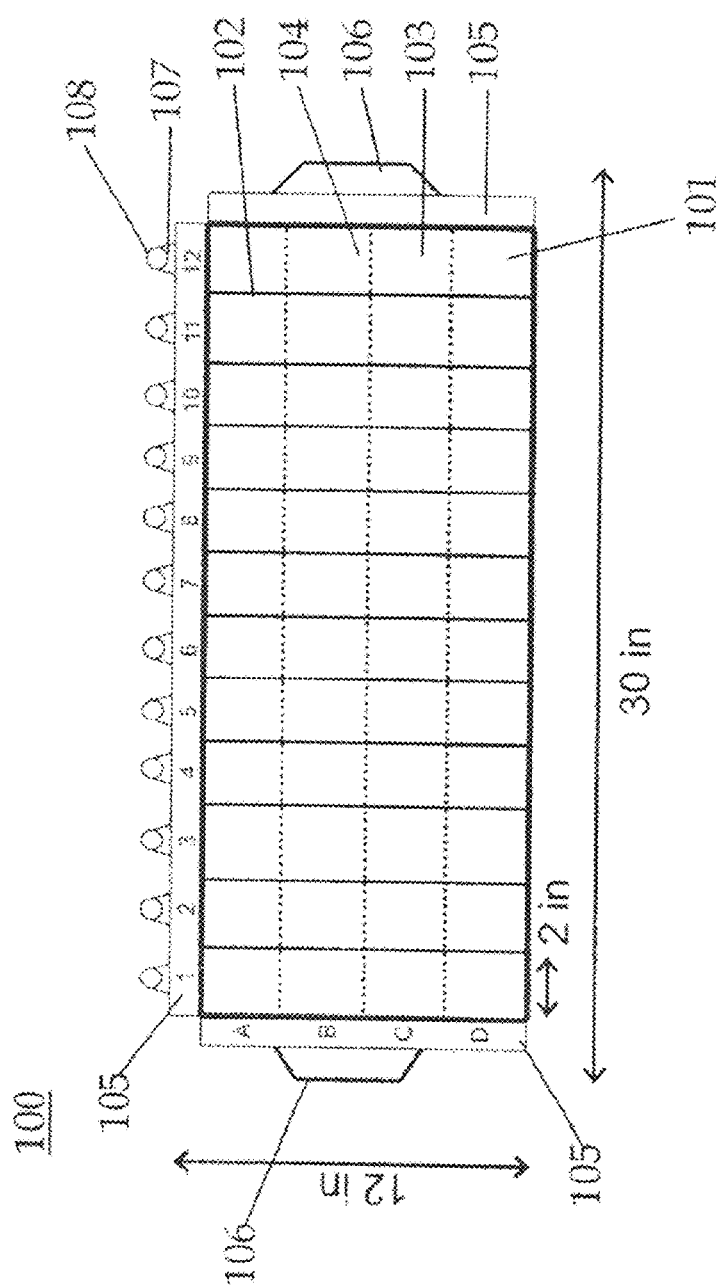
FIG. 1 is a top plan view drawing of a tank in accordance with one embodiment of the present invention.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including but not limited to. To facilitate understanding, like reference numerals have been used, where possible, to designate like elements common to the figures.

DETAILED DESCRIPTION

In the following detailed description, numerous specific details are set forth in order to provide a thorough understanding of embodiments or other examples described herein. In some instances, well-known methods, procedures, components and circuits have not been described in detail, so as to not obscure the following description.

Further, the examples disclosed are for exemplary purposes only and other examples may be employed in lieu of, or in combination with, the examples disclosed. It should also be noted the examples presented herein should not be construed as limiting of the scope of embodiments of the present disclosure, as other equally effective examples are possible and likely.

FIG. 1 is a top plan view drawing of a tank 100 according to one embodiment of the present invention. The tank 100 is divided into twelve compartments 101 by compartment dividers 102. The compartments 101 are further divided into forty-eight sub-compartments 103 by sub-compartment dividers 104. The compartments 101 and sub-compartments 103 allow researchers to isolate individual or groups of zebrafish from each other during the screening process in an efficient use of space and water. The tank 100 may be constructed of a sturdy material capable of housing an aquatic specimen. For example, the material of the tank 100 may be plastic. The tank 100 and components may be constructed by any suitable means, including but not limited to injection mold processes. Alternatively, the material of the tank 100 may be metal, wood, glass, and the like, or any combination thereof. The tank 100 has ledges 105 that provide space for such purposes as labeling of columns and rows for identification of sub-compartments 103. The ledges 105 can also serve as handles to transport the tank 100. The tank 100 may also have separate handles 106 to allow for a sturdier grip when transporting the tank 100.

The tank 100 is divided into twelve compartments 101 by compartment dividers 102. The dotted lines in the FIG. 1 illustrate removable dividers/baffles. The compartment dividers 102 may be permanently attached to the walls of tank 100 by any adhesive, such as glue, epoxy, and the like, or any combination thereof, or by other fastening means, such as nails, screws, bolts, and the like, or any combination thereof. Alternatively, the compartment dividers 102 may be removable. For example, there may be slots at the ends of each compartment 101 for the compartment dividers 102 to slide in and out of. The slots may be formed by protrusions from the walls of tank 100 or by grooves in the walls of tank 100. The compartments 101 may or may not be equally spaced. The compartment dividers 102 may be constructed of a sturdy material that may or may not be the same as the material of tank 100. For example, the material of the compartment dividers 102 may be plastic. Alternatively, the material of the compartment dividers 102 may be metal, wood, glass, and the like, or any combination thereof.

Each compartment 101 is further divided into as many as four sub-compartments 103 by sub-compartment dividers 104. Similar to the compartment dividers 102, the sub-compartment dividers 104 may be permanently attached to the walls of tank 100 by any adhesive, such as glue, epoxy, and the like, or any combination thereof, or by other fastening means, such as nails, screws, bolts, and the like, or any combination thereof. Likewise, the sub-compartment dividers 104 may be removable. For example, there may be slots built in to the walls of tank 100 and the compartment dividers 102 at specific intervals for the sub-compartment dividers 104 to slide in and out of. The slots may be formed by protrusions from or grooves in the walls of tank 100 and/or the compartment dividers 102. The sub-compartments 103 may or may not be equally spaced. The sub-compartment dividers 104 may be constructed of a sturdy material that may or may not be the same as the material of the tank 100 or of the compartment dividers 102. For example, the material of the sub-compartment dividers may be plastic. Alternatively, the material of the compartment dividers 102 may be metal, wood, glass, and the like, or any combination thereof.

Each compartment 101 has a collection channel 107 at one end of that compartment 101. The collection channel 107 ends in a downspout 108 to empty water from the compartment 101 to a drainage system, where the water may drain to a sewer system or alternatively be recycled. The collection channel 107 may be tapered to allow for the water in the compartment 101 to more easily flow to the downspout 108. The downspout 108 may be of any material suitable for water, such as glass, rubber, plastic, and the like. There should be a water-tight seal between the collection channel 107 and the downspout 108 to prevent any leakage of water. This can be accomplished by any means known to a person skilled in the art, such as a gasket, epoxy, and the like, or any combination thereof.

Figure 2:
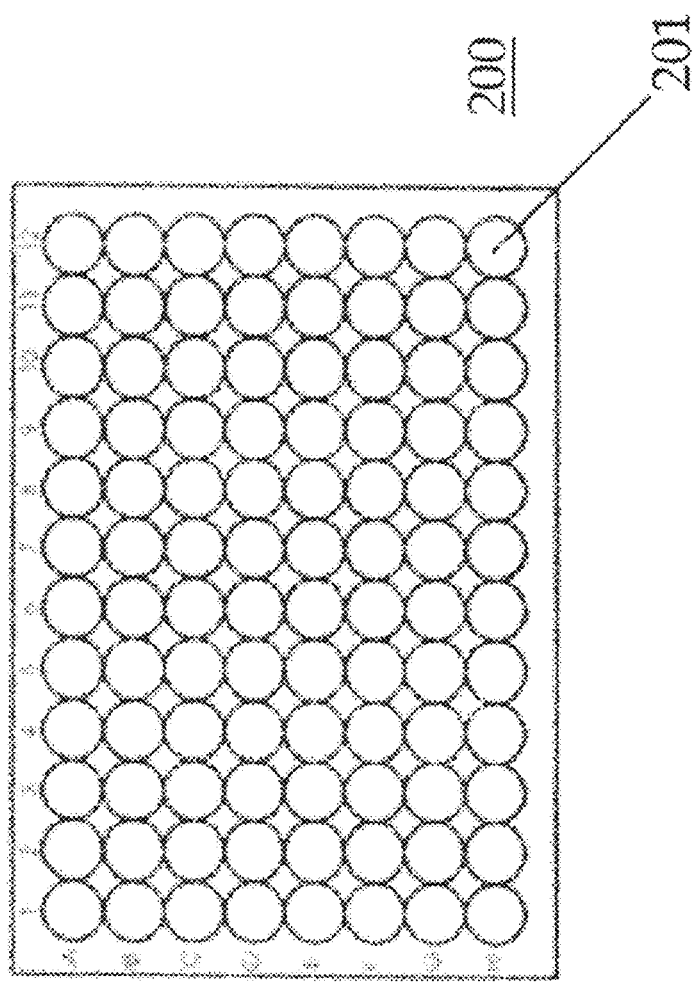
FIG. 2 is a top plan view drawing of a 96 well plate in accordance with one embodiment of the present invention.

FIG. 2 is a top plan view of a 96 well plate 200. In an embodiment, the 96 well plate 200 is of 8*12 matrix. Further, as shown, the 96 well plate 200 includes ninety-six wells, such as a well 201. Furthermore, the 96 well plate 200 may be of standard kind made by any manufacturer.

Figure 3:
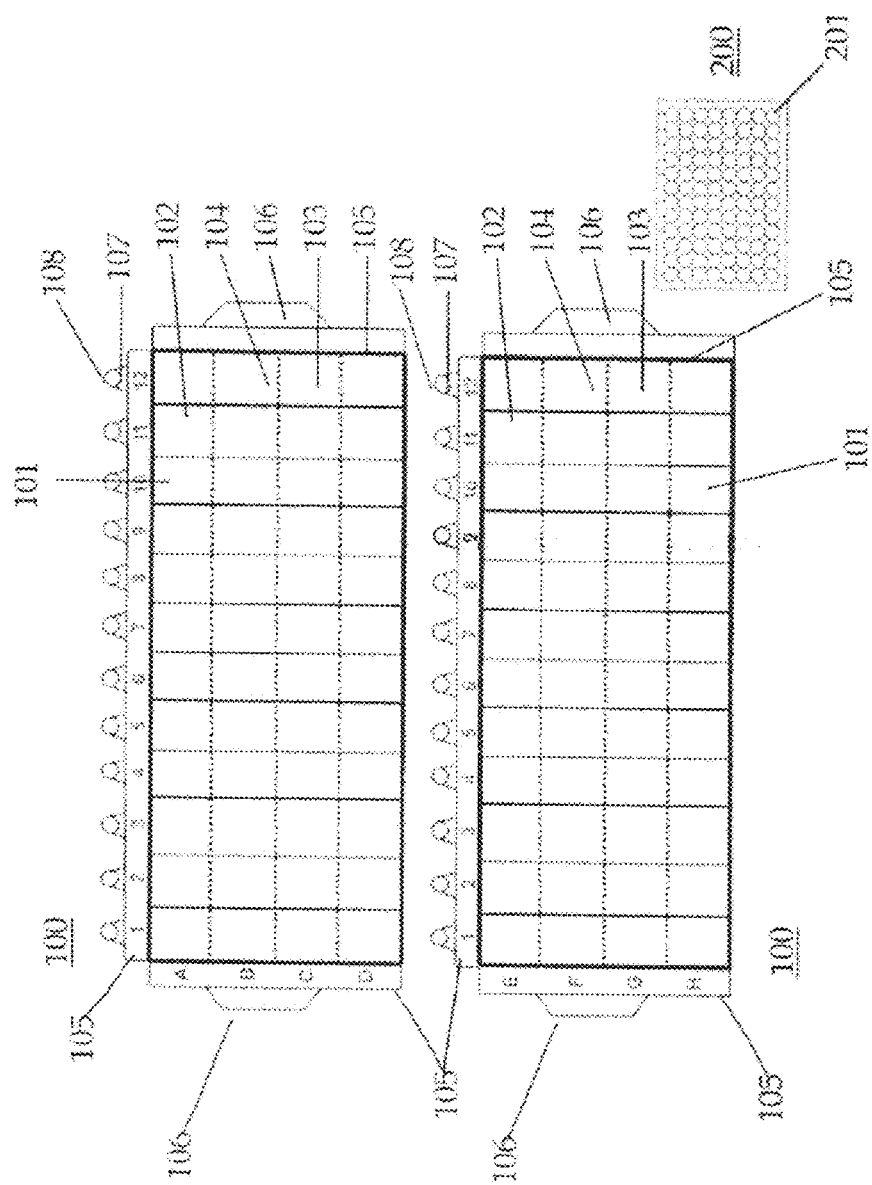
FIG. 3 is a top plan view drawing of two of the tanks of FIG. 1 and the 96 well plate of FIG. 2 in accordance with one embodiment of the present invention.

FIG. 3 is a top plan view drawing of two of the tanks 100 depicted in FIG. 1 and described above, and a 96 well plate 200 with ninety-six wells. The two tanks 100 with all the compartment dividers 102 and sub-compartment dividers 104 will have a total of ninety-six sub-compartments 103. When the two tanks are arranged in the configuration as depicted in FIG. 14, the layout of the sub-compartments 103 will mimic that of the 96 well plate 200.

Figure 4:
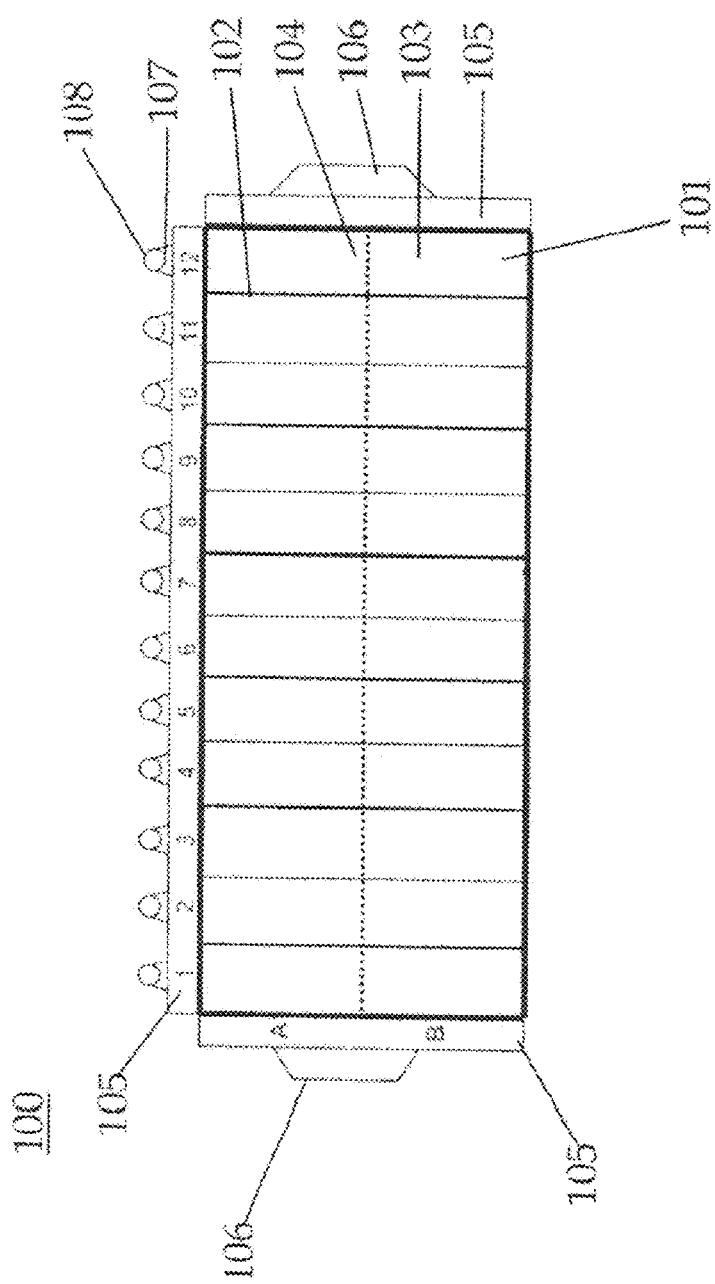
FIG. 4 is a top plan view drawing of a tank in accordance with one embodiment of the present invention.

FIG. 4 is a top plan view drawing of the tank 100 where each compartment 101 is divided into only two sub-compartments 103. With more space per sub-compartment 103 than the arrangement depicted in FIG. 1, this arrangement allows researchers the flexibility of screening more than one fish per sub-compartment 103 with more space than the arrangement depicted in FIG. 1. This arrangement is particularly useful for holding pairs of zebrafish while their embryos are screened for mutations or trans-genesis.

Figure 5:
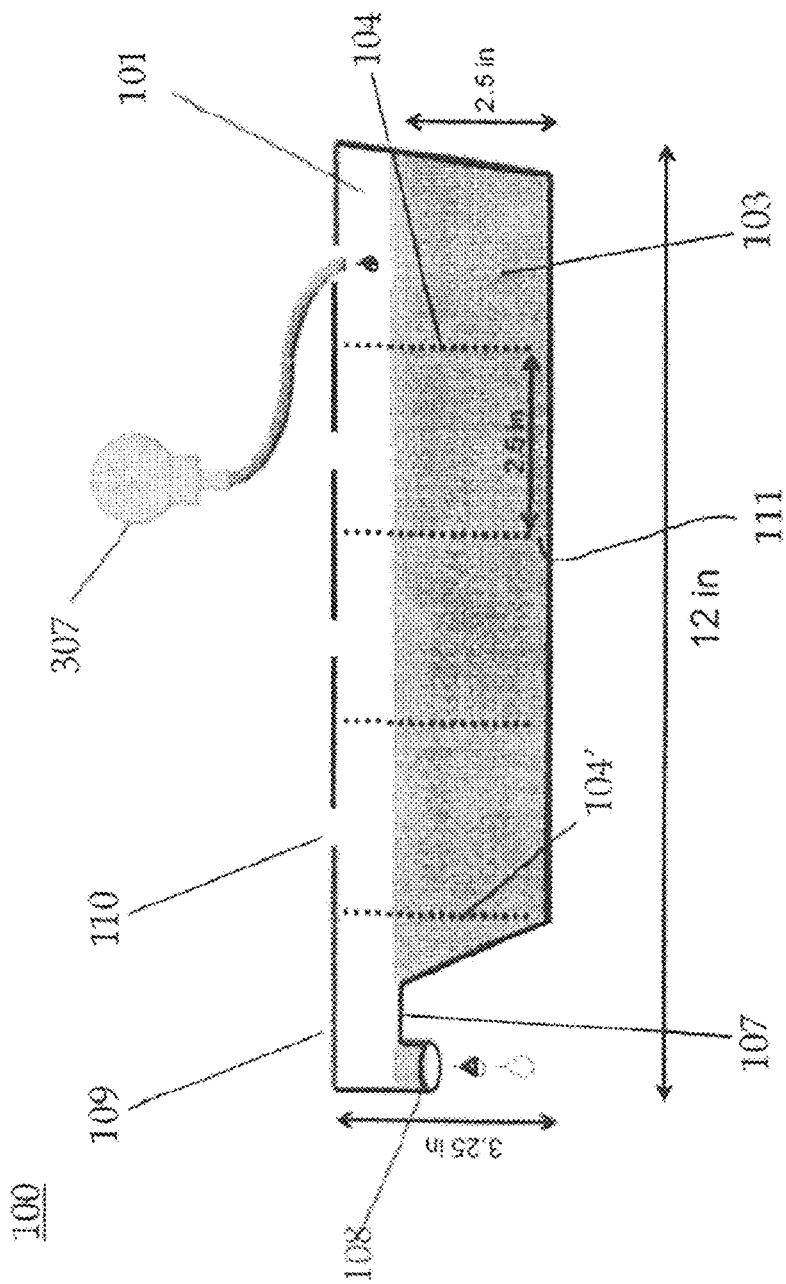
FIG. 5 is a side elevation view drawing of a tank filled with water and connected to a water source in accordance with one embodiment of the present invention.

FIG. 5 is a side elevation view drawing of the tank 100, more specifically, one compartment 101. A lid 109 is covering the compartment 101. The lid 109 has an aperture 110 over each of the sub-compartments 103. The apertures 110 may be any size and shape, and may serve as feeding holes for the fish. Alternatively, the apertures 110 may serve as openings for introducing water into the compartment 101 from the water source 307. The water source 307 may introduce water to the compartment 101 through any one of the apertures 110. Each aperture 110 may have its own flap or lid to prevent foreign material from entering the compartment 101 when the aperture 110 is not being utilized. The lid 109 may or may not be made of the same material as the tank 100, compartment dividers 102, and/or sub-compartment dividers 104.

To allow for a constant flow of water from one sub-compartment 103 to another, the sub-compartment dividers 104 do not touch the base of the tank 100 creating gaps 111. This may be accomplished by a lip on which the sub-compartment dividers 104 rest. The lip will be positioned at a set height above the base of the tank 100 and at the bottom of the slots or grooves in which the sub-compartment dividers 104 slide in and out, such that the fish will be unable to swim under the sub-compartment dividers 104 to get from one sub-compartment 103 to another. Additionally, the sub-compartment dividers 104 may have apertures in them to further allow for the constant flow of water, especially in the situation where the gaps 111 become clogged from debris. The apertures will be sized small enough such that the fish will be unable to swim through them to get from one sub-compartment 103 to another. Additionally, compartmental dividers may also have a gap at the bottom to allow water to easily flow from one compartment to another (as shown further in FIG. 14A).

At the end of the compartment 101 where the collection channel 107 and downspout 108 are located, there is an additional divider 104' that separates the compartment 101 from the collection channel 107 and downspout 108. The divider 104' will be identical to the sub-compartment dividers 104. The divider 104' should be in place whenever there are fish in a compartment 101 so that the fish will be prevented from entering the downspout 108 and ultimately the drainage system. However, the divider 104' may be removable in a similar fashion as the sub-compartment dividers 104.

Figure 6:
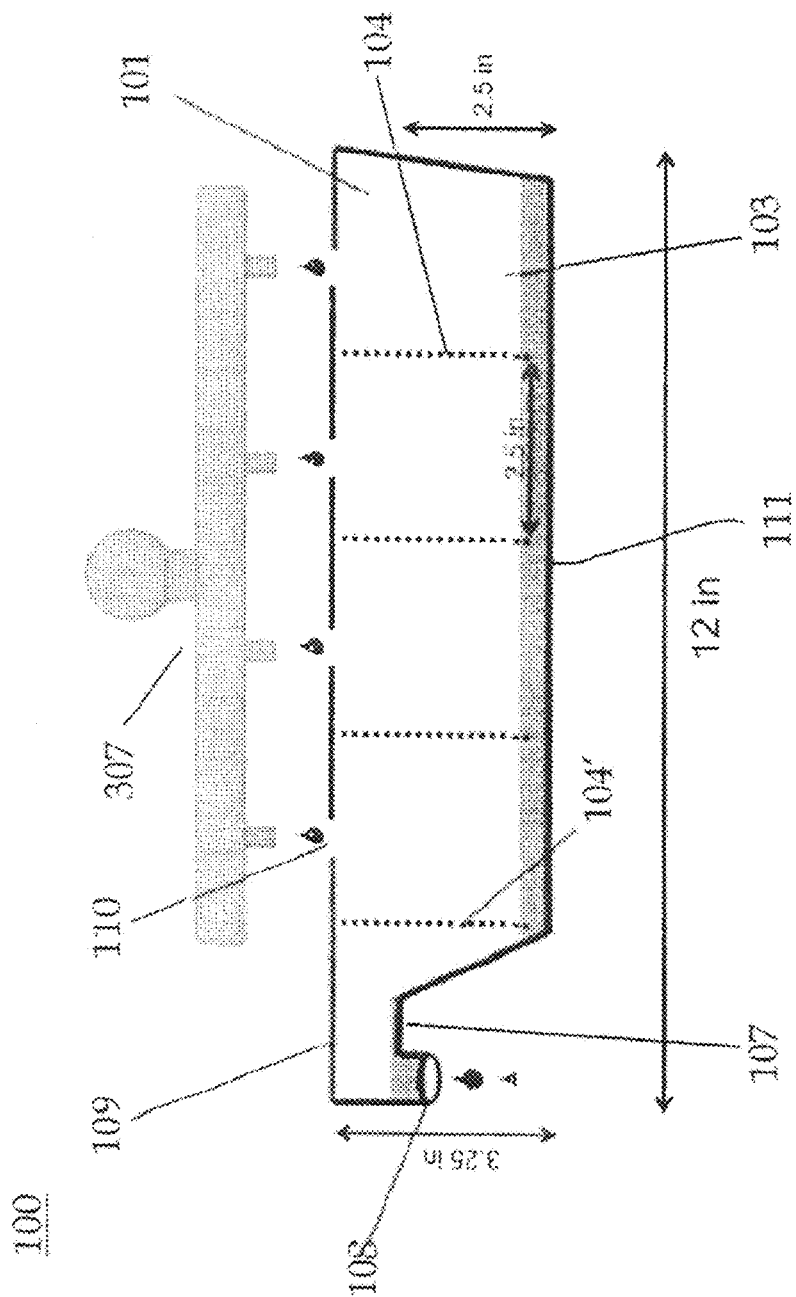
FIG. 6 is a side elevation view drawing of a tank filled with water and connected to a source of water in accordance with one embodiment of the present invention.
Figure 7:
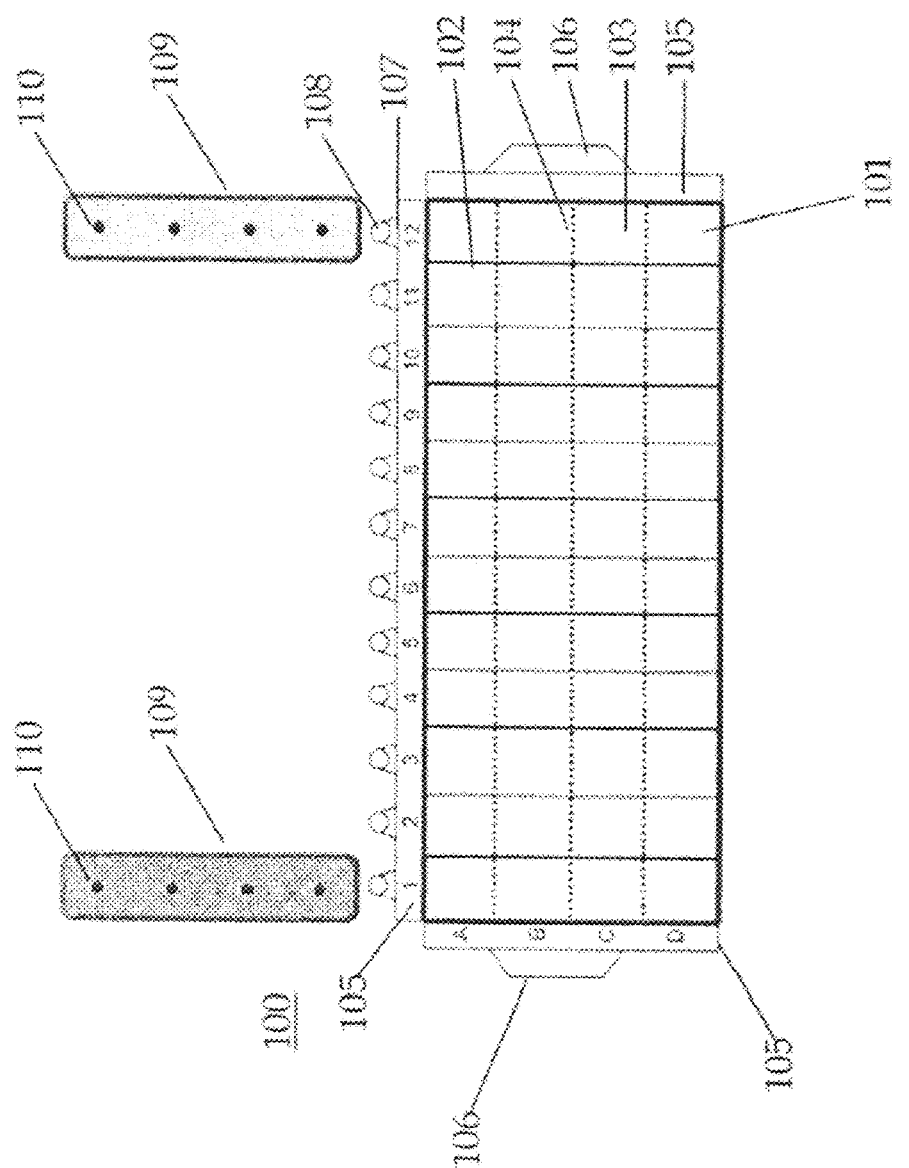
FIG. 7 is a top plan view drawing of the tank of FIG. 1 and lids in accordance with one embodiment of the present invention.
Figure 8:
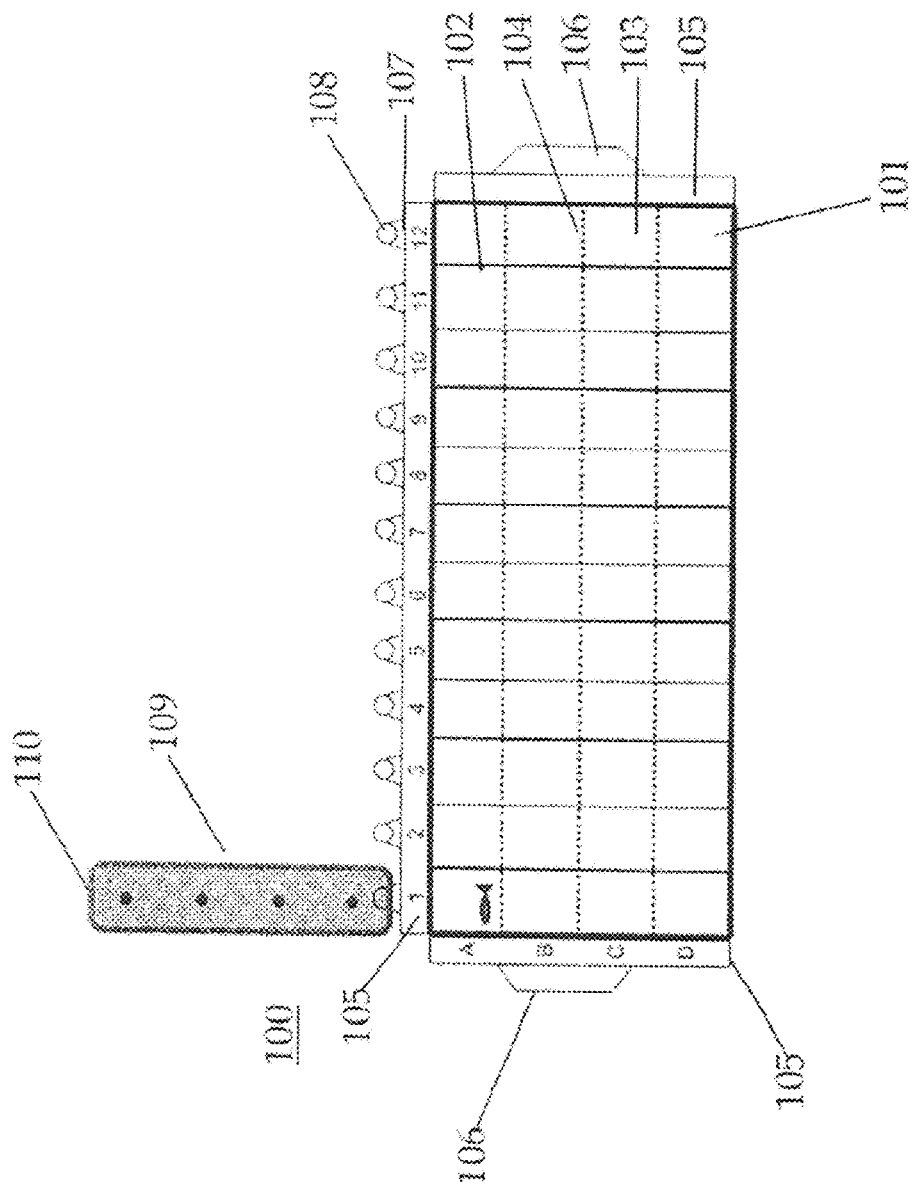
FIG. 8 is a top plan view drawing of the tank of FIG. 1, illustrating the step of applying one lid to one compartment in accordance with one embodiment of the present invention.
Figure 9:
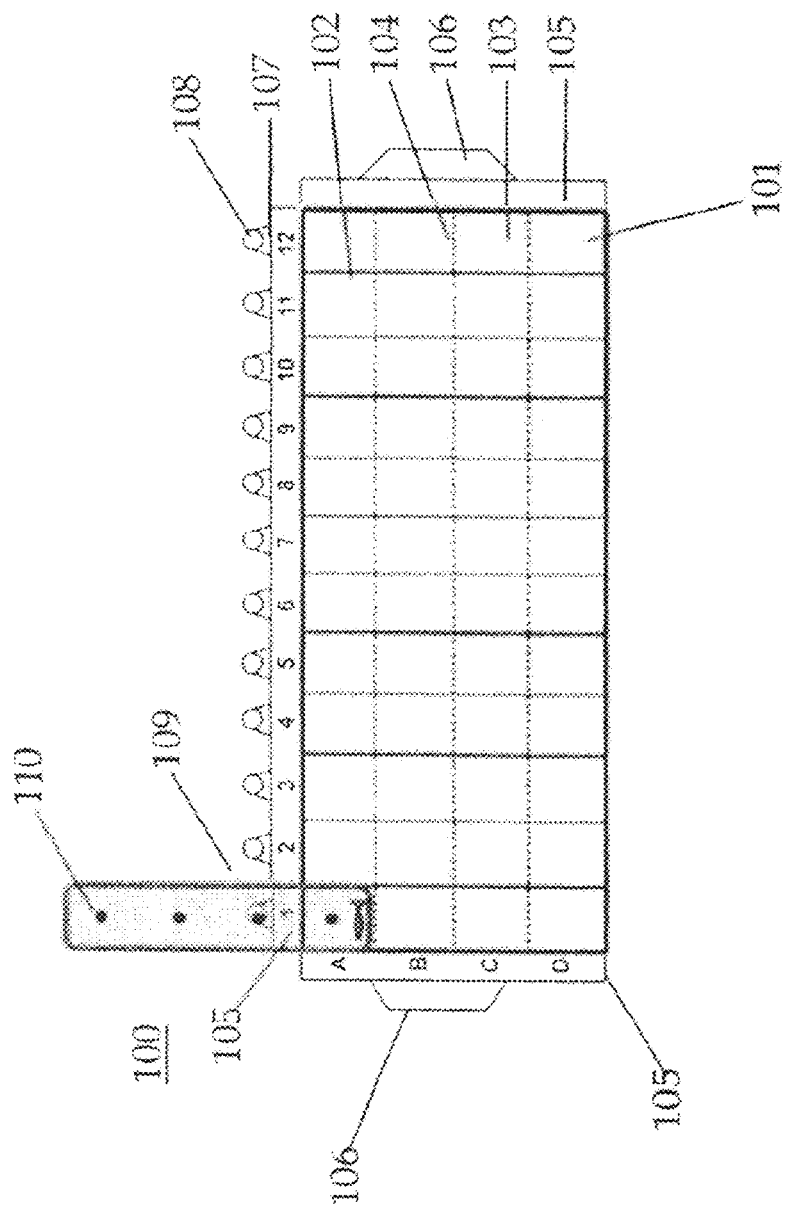
FIG. 9 is a top plan view drawing of the tank of FIG. 1, illustrating the step of applying one lid to one compartment in accordance with one embodiment of the present invention.
Figure 10:
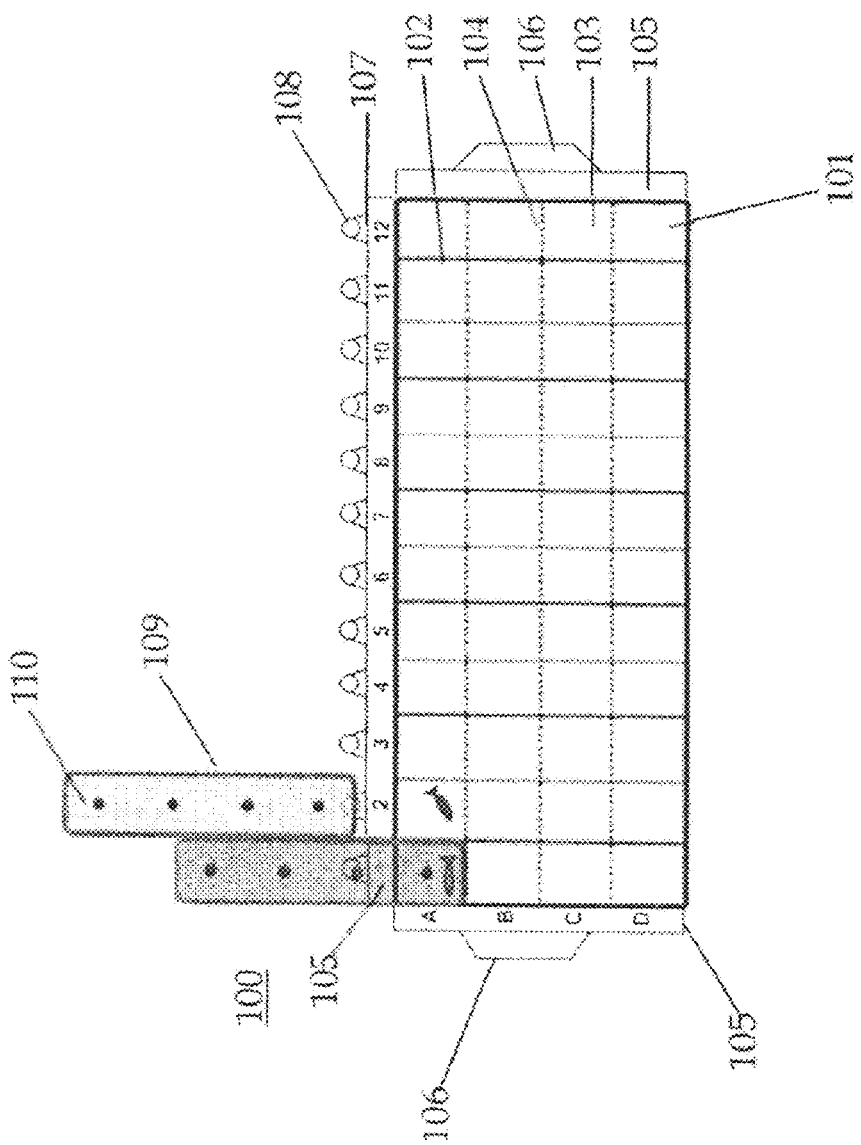
FIG. 10 is a top plan view drawing of the tank of FIG. 1, illustrating the step of applying two lids to two compartments in accordance with one embodiment of the present invention.
Figure 11:
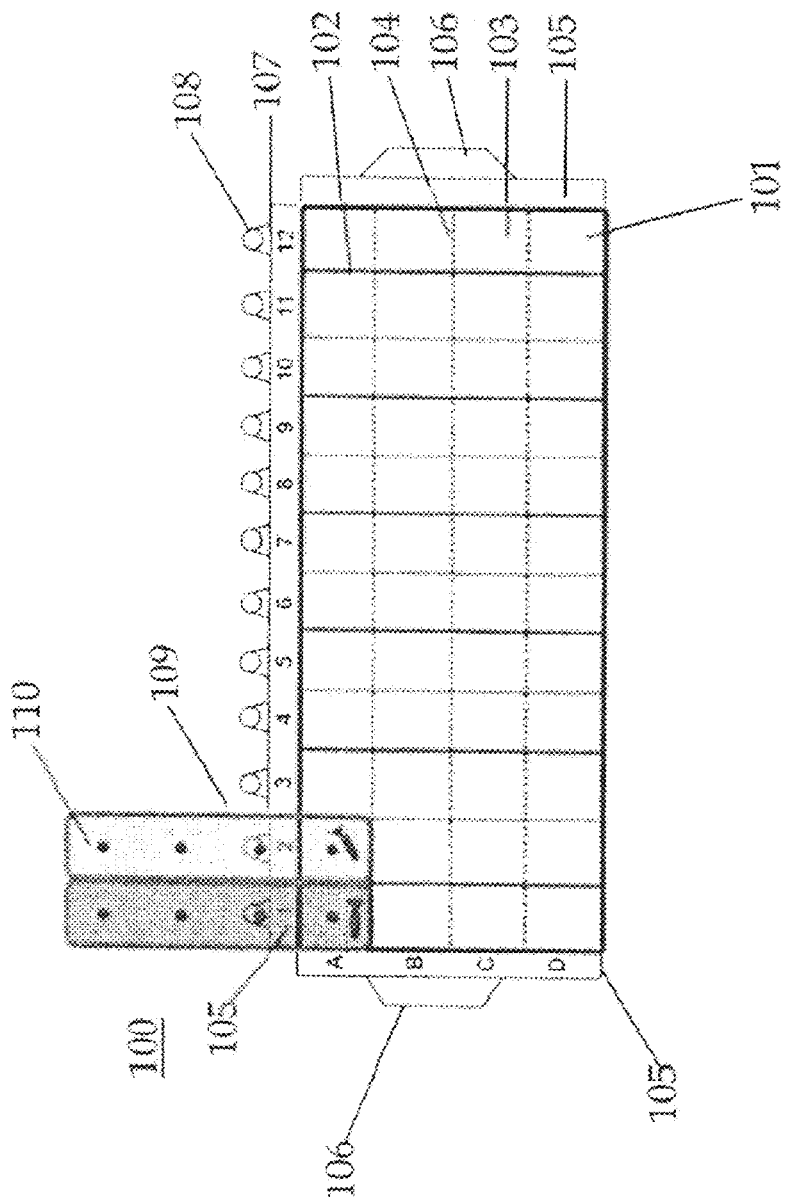
FIG. 11 is a top plan view drawing of the tank of FIG. 1, illustrating the step of applying two lids to two compartments in accordance with one embodiment of the present invention.
Figure 12:
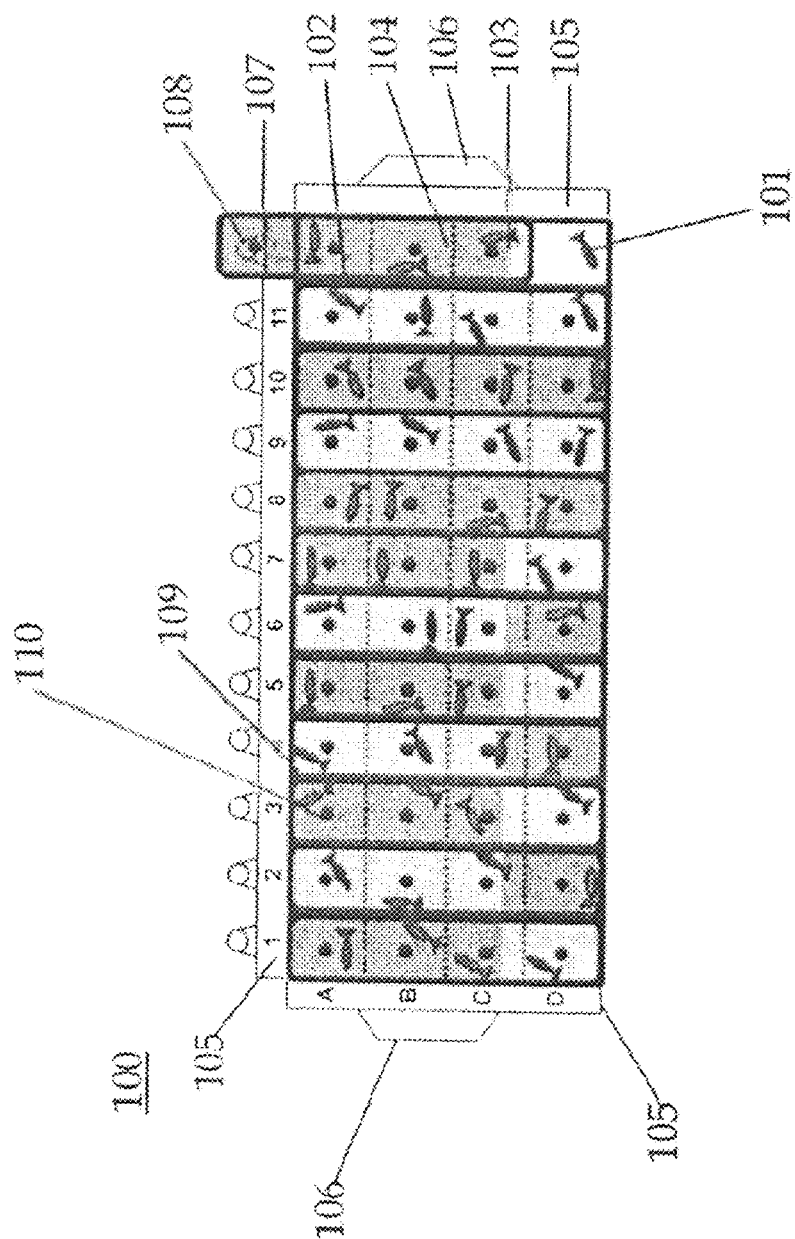
FIG. 12 is a top plan view drawing of the tank of FIG. 1, illustrating the step of applying a plurality of lids to the compartments in accordance with one embodiment of the present invention.
Figure 13:
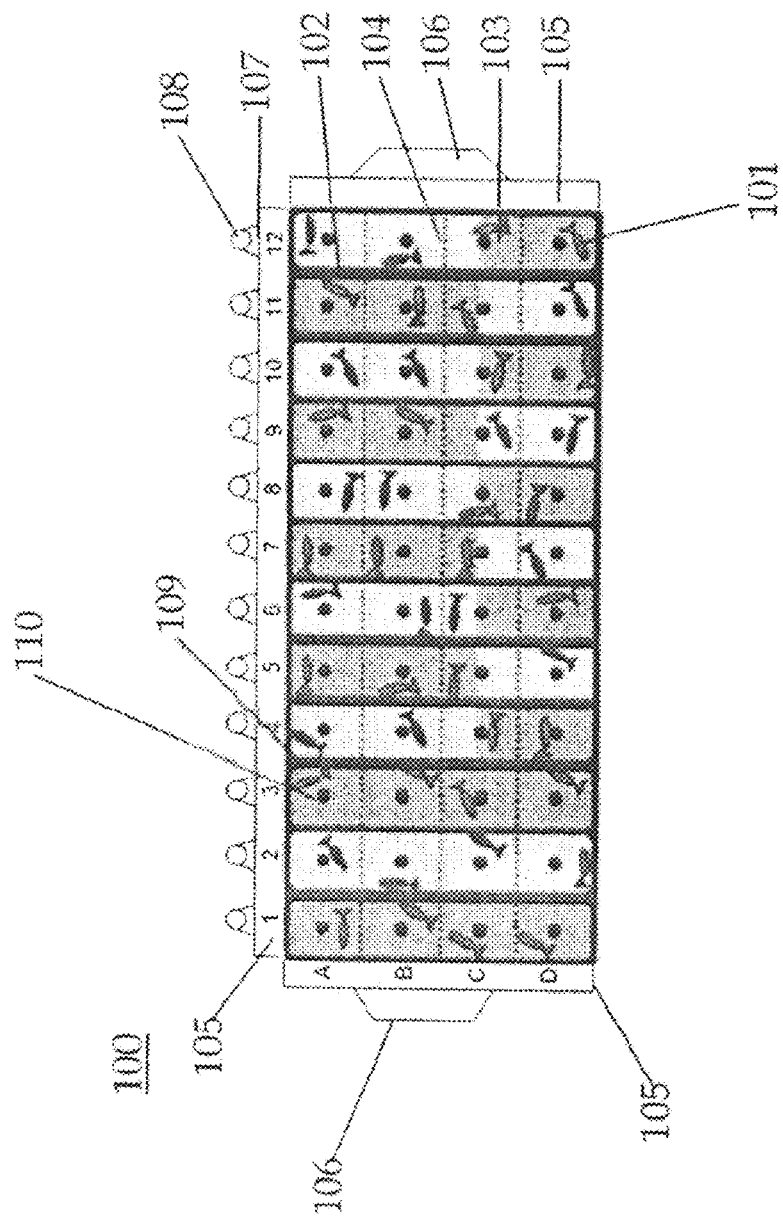
FIG. 13 is a top plan view drawing of the tank of FIG. 1, with a plurality of sub-compartment dividers and compartment lids in place in accordance with one embodiment of the present invention.

FIG. 6 is another side elevation view drawing of the tank 100 and compartment 101 according to another embodiment of the present invention. In this embodiment, the water source 307 introduces water to each of the sub-compartments 103 individually and at the same time through each of the apertures 110 in the lid 109. The lid 109 does not have to be in place while the water is being introduced to the sub-compartments 103.

FIGS. 7 through 13 are top plan view drawings of the tank 100 depicted in FIG. 1 and lids 109 for each compartment 101, and illustrate the step of applying lids 109 to the compartments 101. The lid 109 can be applied to the compartment 101 by any means known to a person skilled in the art. For example, the lid 109 can slide into slots built into the top of the compartment dividers 102 and the walls of tank 100. Alternatively, the top edges of the compartment dividers 102 and the walls of tank 100 can have notches cut out that span the entire length of each compartment 101, creating a ledge for the lid 109 to rest on. Each lid 109 has four apertures 110 such that when the lid 109 is fully covering the compartment 101, an aperture 110 will be above each sub-compartment 103. The apertures 110 can serve as feeding holes for the fish in the sub-compartments 103, or as an entrance for introducing water into the compartments 101. The apertures 110 may be any size or shape. Alternatively, the lids 109 may have no apertures 110.

Figure 14A:
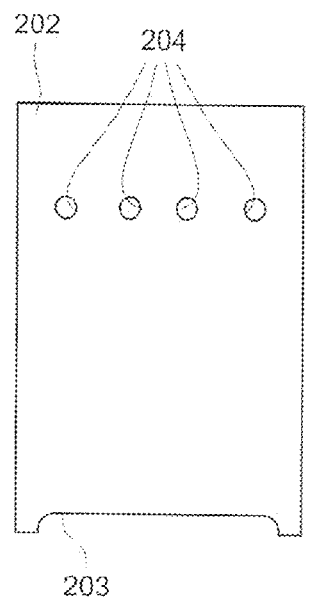
FIGS. 14A and 14B are front elevation view of a divider, and front elevation view of a tank with plurality of such dividers, respectively, in accordance with an embodiment of the present invention.
Figure 14B:
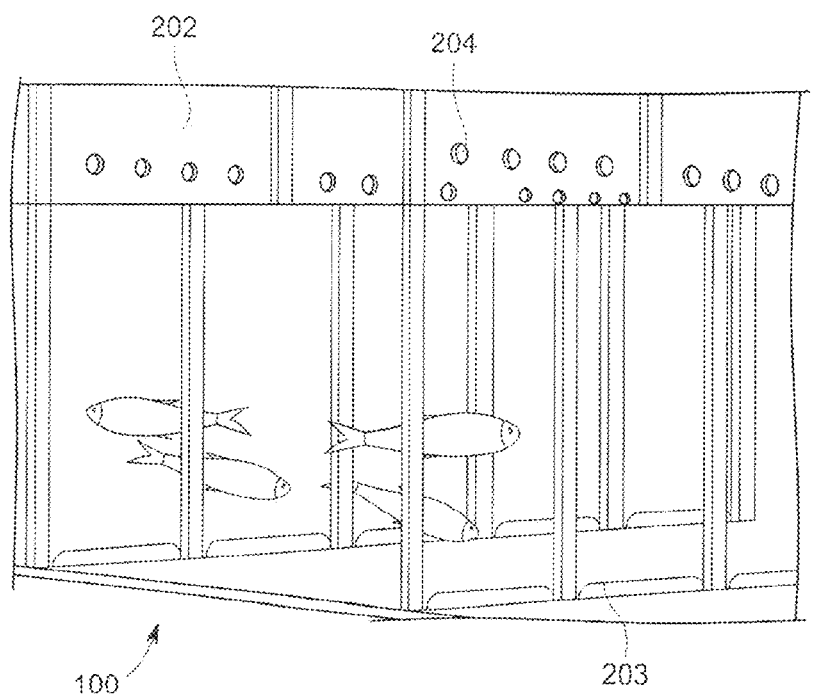

FIGS. 14A and 14B are front elevation view of a divider 202, and front elevation view of the tank 100 with plurality of such dividers 202, respectively. The divider 202 has a gap 203 at its bottom. The gap 203 in the divider 202 allows water, food, and waste to pass through. When the divider 223 is placed into a tank, such as tank 100 (as shown in FIG. 14B), the gap 203 in the divider 202 allows water, food, and waste to flow from one compartment to other compartments of the tank 100.

Additionally, as shown in FIG. 14A, the divider 202 also has plurality of holes 204 at its top section. The holes 204 in the divider 202 enable water flow via the divider 202. When the divider 202 is placed into a tank, such as tank 100 (as shown in FIG. 14B), the holes 204 in the divider 202 makes a passage for the water to pass to adjacent compartments. Thereby, the holes 204 ensure proper flow of water in compartments of the tank 100 even if the gap 203 of any divider 202 gets clogged.

Figure 15A:
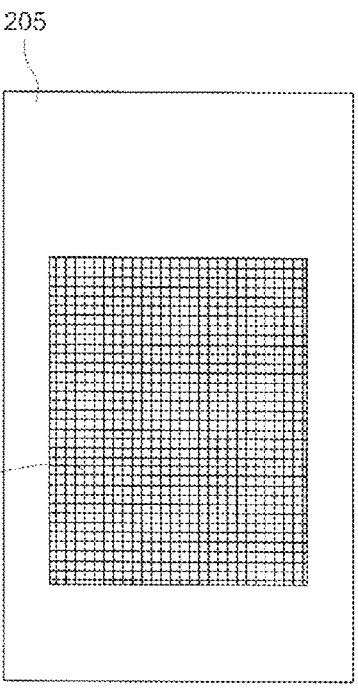
FIGS. 15A and 15B are front elevation views of a divider having an opening covered by a fine mesh, in accordance with an embodiment of the present invention.
Figure 15B:
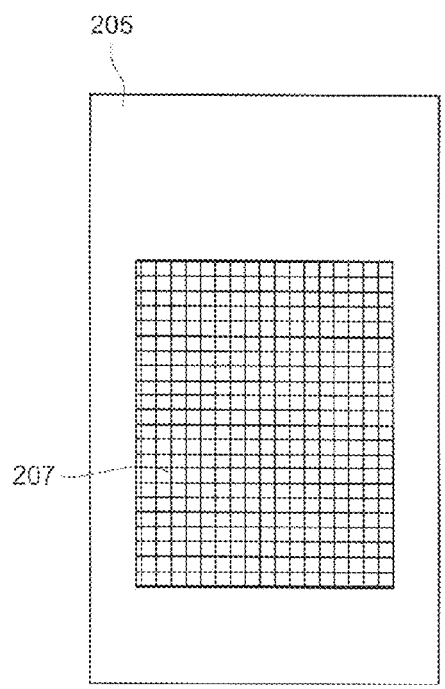

FIGS. 15A and 15B are front elevation views of a divider 205 having an opening (not shown) covered by a fine mesh, such as mesh 206 and 207. Some research requires raising an individual fry or larva separate from other fry or larva because of their unique genetic, morphological, or phenotypic characteristics. According to the state of art technology, the only way to raise an individual fry/larva is by keeping them separately in individual tanks. However, by using the tank with the dividers 205 having an opening covered by fine mesh, such as mesh 206 and 207, researchers can raise individual larva or fry in same tank having different compartments.

In an exemplary embodiment of the present invention, the divider 205 (as shown in FIG. 15A) may have a fine mesh 206 of 800 micron. In another exemplary embodiment of the present invention, the divider 205 (as shown in FIG. 15B) may have a fine mesh 207 of 400 micron. Researchers may select any of the mesh of either 400 micron or 800 micron for the divider 205, based on research requirements.

Figure 16:
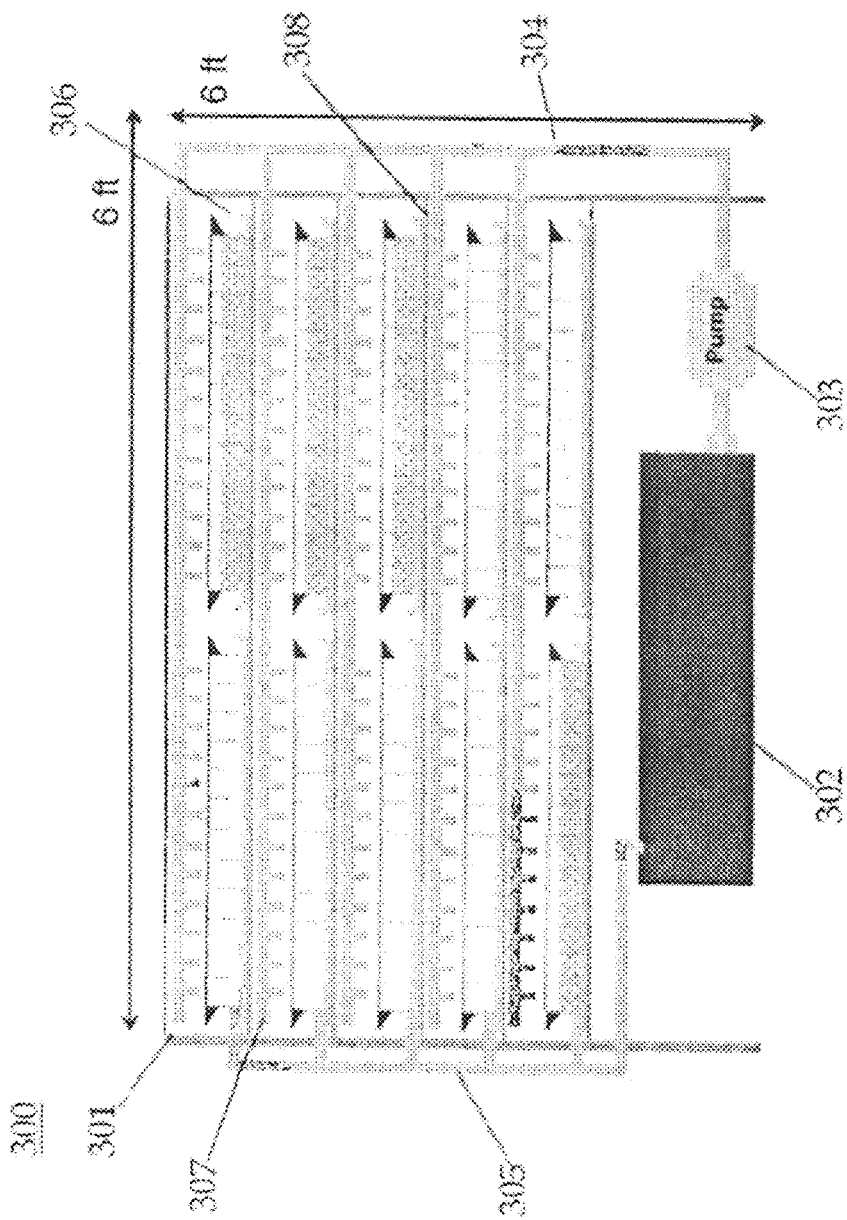
FIG. 16 is a front elevation view drawing of a plurality of tanks housed on a housing rack in accordance with one embodiment of the present invention.

FIG. 16 is a front elevation view drawing of the system 300 according to one embodiment of the present invention. The system comprises a multitude of tanks 100, a housing rack 301, a water collection tank 302, a pump 303, water distribution pipes 304, and water drain pipes 305. The housing rack 301 is standard that may be provided by any manufacturer. Alternatively, the water distribution pipes 304 may come from the city water supply system and the water drain pipes 305 may drain directly to the sewer system in lieu of a water collection tank 302 and pump 303, respectively.

Figure 17:
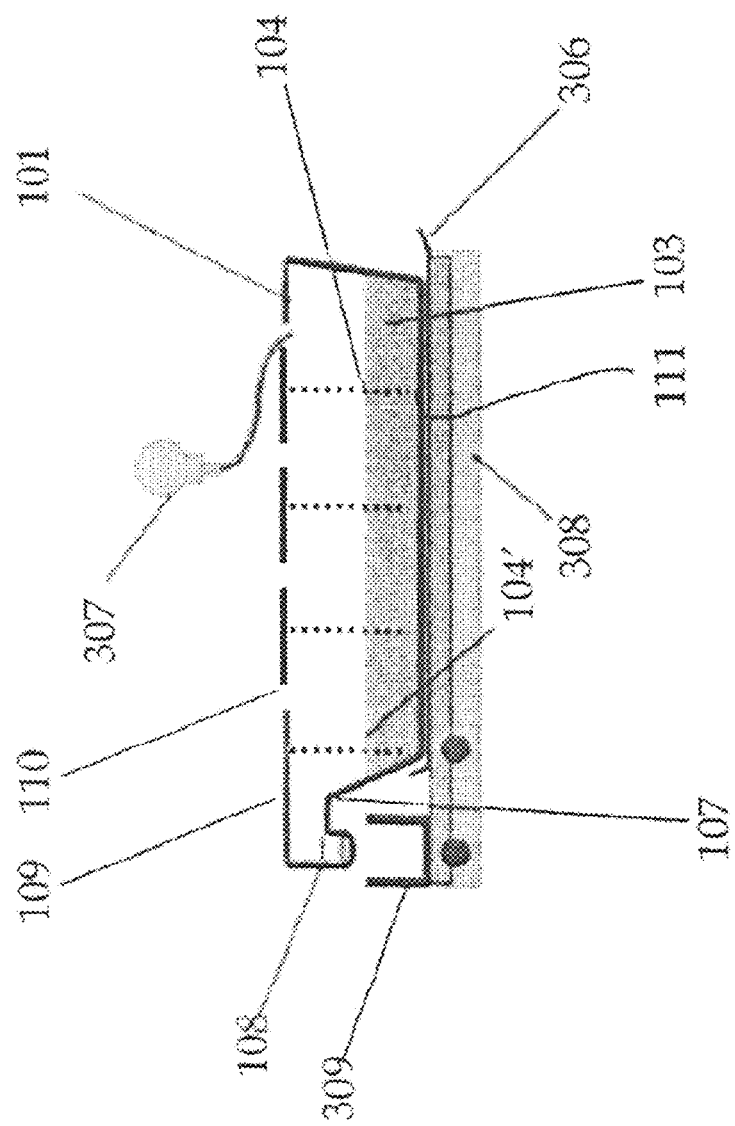
FIG. 17 is a side elevation view drawing of the tank of FIG. 5 positioned on a drawer on a shelf of a housing rack in accordance with one embodiment of the present invention.
Figure 18:
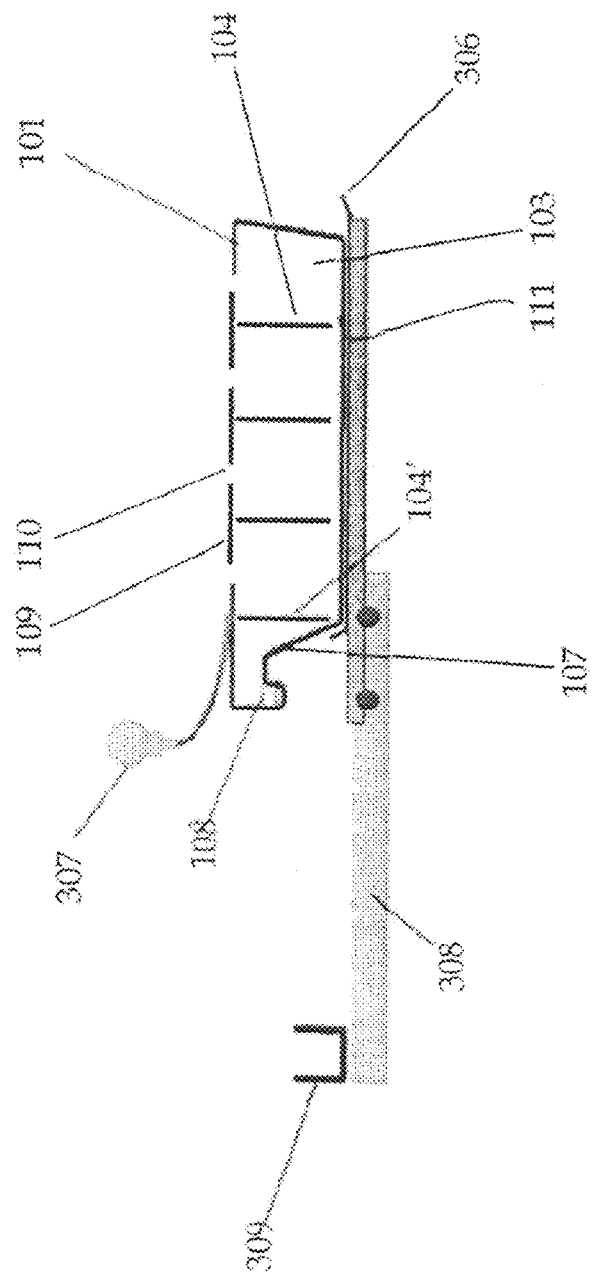
FIG. 18 is a side elevation view drawing of the tank of FIG. 5 positioned on an extended drawer on a shelf of the housing rack in accordance with one embodiment of the present invention.

FIGS. 17 and 18 are side elevation view drawings of a tank 100 on a drawer 306. The drawer 306 is attached to a shelf 308 that is part of the housing rack 301. When the drawer 306 is pushed in, the downspout 108 will be positioned above a drainage trough 309. When the water level reaches a certain level, which is determined by the height of the collection channel 107, the water will empty to the downspout 108 into the drainage trough 309, and ultimately to a water collection tank 302 or alternatively to the sewer system. Therefore, the water source 307 should be turned off when the drawer 306 is extended to prevent water spillage. When the drawer 306 is extended, a researcher will be able to access the tank 100 for any purpose such as testing and/or feeding fish, cleaning the tank, and the like.

Figure 19:
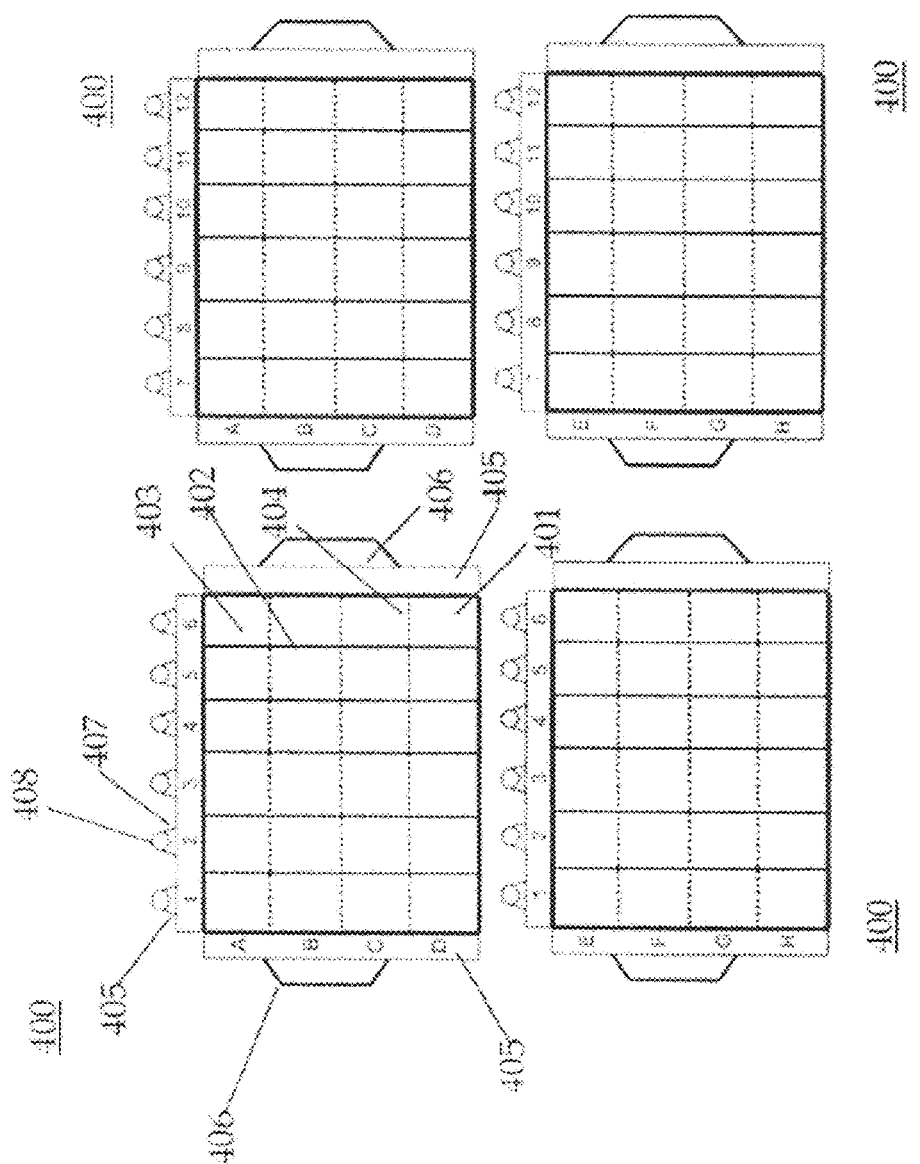
FIG. 19 is a top plan view drawing of four tanks in accordance with one embodiment of the present invention.

FIG. 19 is a top plan view drawing of four tanks 400 according to another embodiment of the present invention. Each tank 400 is divided into six compartments 401 by compartment dividers 402. The compartments 401 are further divided into twenty-four sub-compartments 403 by sub-compartment dividers 404. With four tanks 400 arranged in the configuration depicted in FIG. 19, the layout of the sub-compartments 403 will mimic that of a 96 well plate.

Each tank 400 may be constructed of a sturdy material. For example, the material of the each tank 400 may be plastic. Alternatively, the material of each tank 400 may be metal, wood, glass, and the like, or any combination thereof. Each tank 400 has ledges 405 that provide space for such purposes as labeling of columns and rows for identification of sub-compartments 403. The ledges 405 can also serve as handles to transport each tank 400. Each tank 400 may also have separate handles 406 to allow for a sturdier grip when transporting each tank 400.

Each tank 400 is divided into six compartments 401 by compartment dividers 402. The compartment dividers 402 may be permanently attached to the walls of each tank 400 by any adhesive, such as glue, epoxy, and the like, or any combination thereof, or by other fastening means, such as nails, screws, bolts, and the like, or any combination thereof. Alternatively, the compartment dividers 402 may be removable. For example, there may be slots at the ends of each compartment 401 for the compartment dividers 402 to slide in and out of. The slots may be formed by protrusions from the walls of tank 400 or by grooves in the walls of each tank 400. The compartments 401 may or may not be equally spaced. The compartment dividers 402 may be constructed of a sturdy material that may or may not be the same as the material of each tank 400. For example, the material of the compartment dividers 402 may be plastic. Alternatively, the material of the compartment dividers 402 may be metal, wood, glass, and the like, or any combination thereof.

Each compartment 401 is further divided into as many as four sub-compartments 403 by sub-compartment dividers 404. Similar to the compartment dividers 402, the sub-compartment dividers 404 may be permanently attached to the walls of tank 400 by any adhesive, such as glue, epoxy, and the like, or any combination thereof, or by other fastening means, such as nails, screws, bolts, and the like, or any combination thereof. Likewise, the sub-compartment dividers 404 may be removable. For example, there may be slots built in to the walls of each tank 400 and the compartment dividers 402 at specific intervals for the sub-compartment dividers 404 to slide in and out of. The slots may be formed by protrusions from or grooves in the walls of each tank 400 and/or the compartment dividers 402. The sub-compartments 403 may or may not be equally spaced. The sub-compartment dividers 404 may be constructed of a sturdy material that may or may not be the same as the material of the tank 400 or of the compartment dividers 402. For example, the material of the sub-compartment dividers 404 may be plastic. Alternatively, the material of the compartment dividers 402 may be metal, wood, glass, and the like, or any combination thereof.

Each compartment 401 has a collection channel 407 at one end of that compartment 401. The collection channel 407 ends in a downspout 408 to empty water from the compartment 401 to a drainage system, where the water may drain to a sewer system or alternatively be recycled. The collection channel 407 may be tapered to allow for the water in the compartment 401 to more easily flow to the downspout 108. The downspout 408 may be of any material suitable for water, such as glass, rubber, plastic, and the like. There should be a water-tight seal between the collection channel 407 and the downspout 408 to prevent any leakage of water. This can be accomplished by any means known to a person skilled in the art, such as a gasket, epoxy, and the like, or any combination thereof.

The arrangement of the sub-compartment dividers 404 will be as depicted in FIG. 5. Each compartment 401 will have a lid as depicted in FIGS. 7 through 13. Furthermore, each tank 400 will be housed on a housing rack as depicted in FIGS. 17 and 18.

Figure 20:
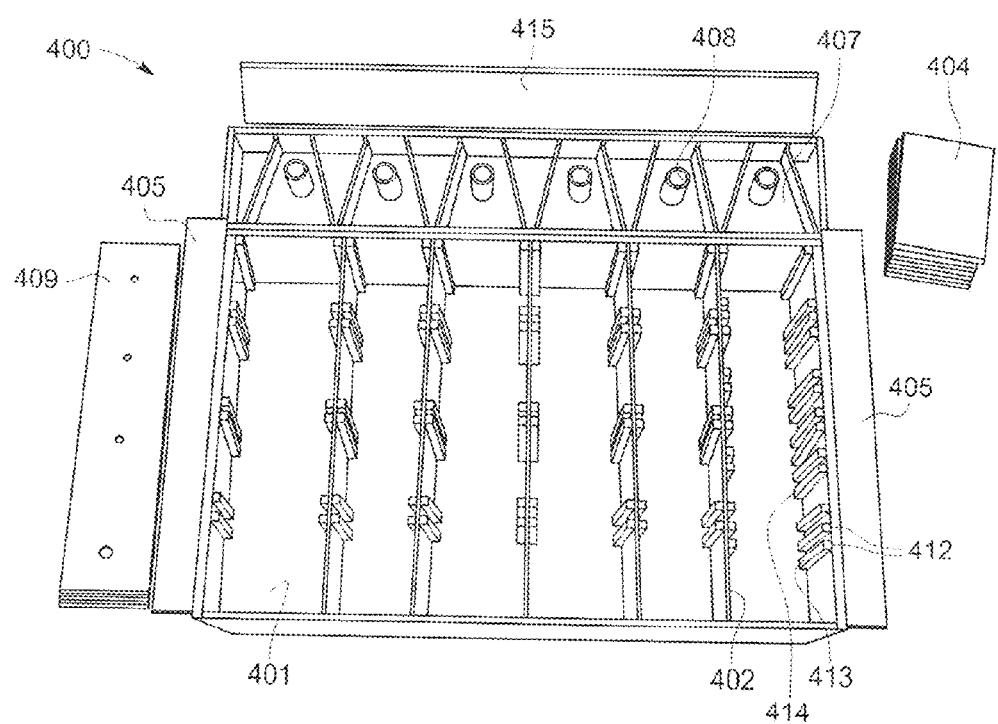
FIG. 20 is a top plan view of a tank with sub-compartment dividers and a back cover in accordance with one embodiment of the present invention.
Figure 21:
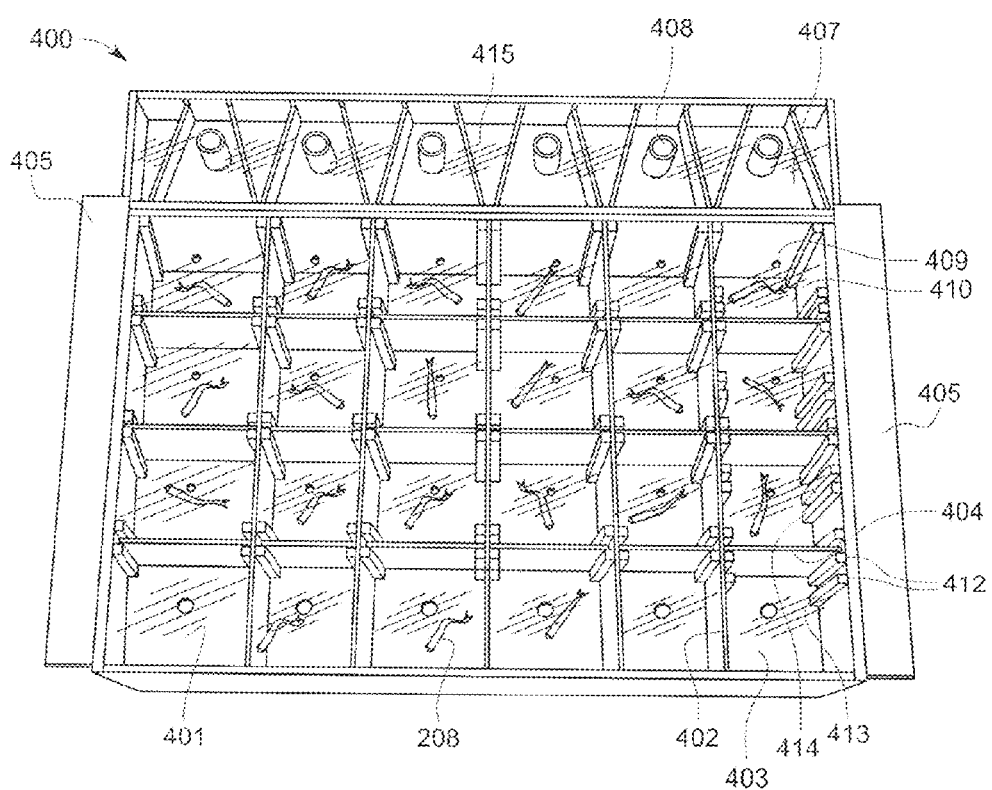
FIG. 21 is a top plan view of the tank of FIG. 18 with sub-compartment dividers and a back cover inserted into the tank in accordance with one embodiment of the present invention.
Figure 22:
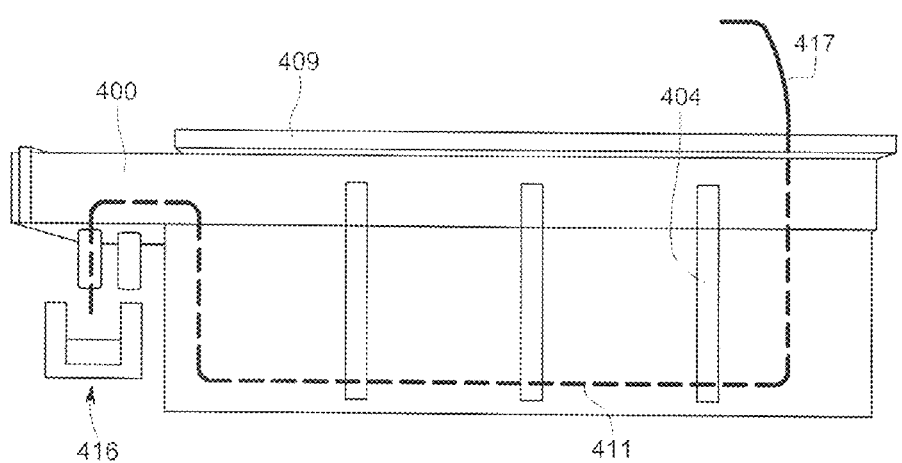
FIG. 22 is a side elevation view of the system illustrating how water flows through a compartment of a tank to a drainage trough on a housing rack in accordance with one embodiment of the present invention.
Figure 23:
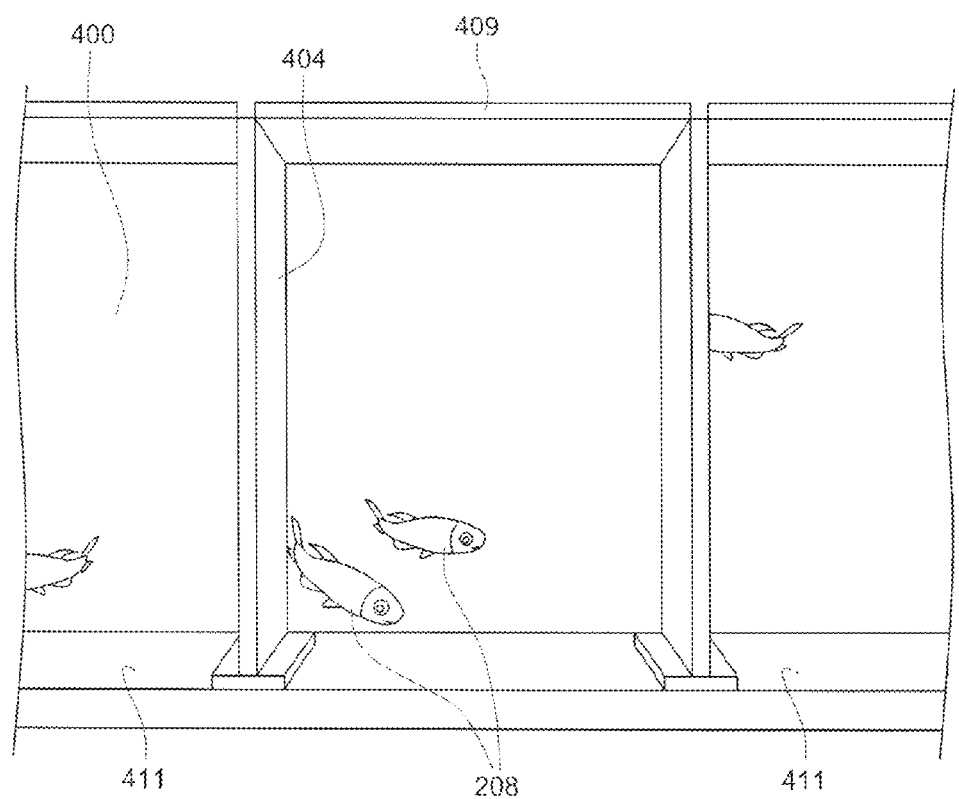
FIG. 23 is an expanded front elevation view of compartments of the tank of FIG. 18 in accordance with one embodiment of the present invention.

FIGS. 20 through 27 illustrate various views of the tank 400 as depicted in FIG. 19. FIG. 20 illustrates a disassembled tank placed on a transport cart. Further as shown in FIGS. 20 and 21, walls of tank 400 and the compartment dividers 402 have protrusions 412 that form slots 413 in which the sub-compartment dividers 404 slide in and out. At the bottom of each slot 413, there is a lip 414 on which the sub-compartment divider 404 sits, leaving a gap 411 (as shown in FIGS. 22 and 23) that allows water to flow from one sub-compartment to another. Furthermore, there is a back cover 415 that covers the collection channels 407 and downspouts 408. The back cover 415 may be applied to the tank 400 by any means known to a person of ordinary skill in the art. For example, there may be slots at the top of the walls of tank 400 in which the back cover 415 may be inserted. The back cover 415 may prevent foreign materials from entering the collection channels 407 and downspouts 408. Additionally, the back cover 415 may provide space for labeling the compartments 401 for identification purposes.

Each compartment 401 has a lid 409. The lid 409 can be applied to the compartment 401 by any means known to a person skilled in the art. For example, the lid 409 can slide into slots built into the top of the compartment dividers 402 and the walls of tank 400. Alternatively, the top edges of the compartment dividers 402 and the walls of tank 400 can have notches cut out that span the entire length of each compartment 401, creating a ledge for the lid 409 to rest on. Each lid 409 has apertures 410 such that when the lid 409 is fully covering the compartment 401, an aperture 410 will be above each sub-compartment 403. The apertures 410 can serve as feeding holes for the fish in the sub-compartments 403, or as an entrance for introducing water into the compartments 401. The apertures 410 may be any size or shape. Alternatively, the lids 409 may have no apertures 410.

Figure 24:
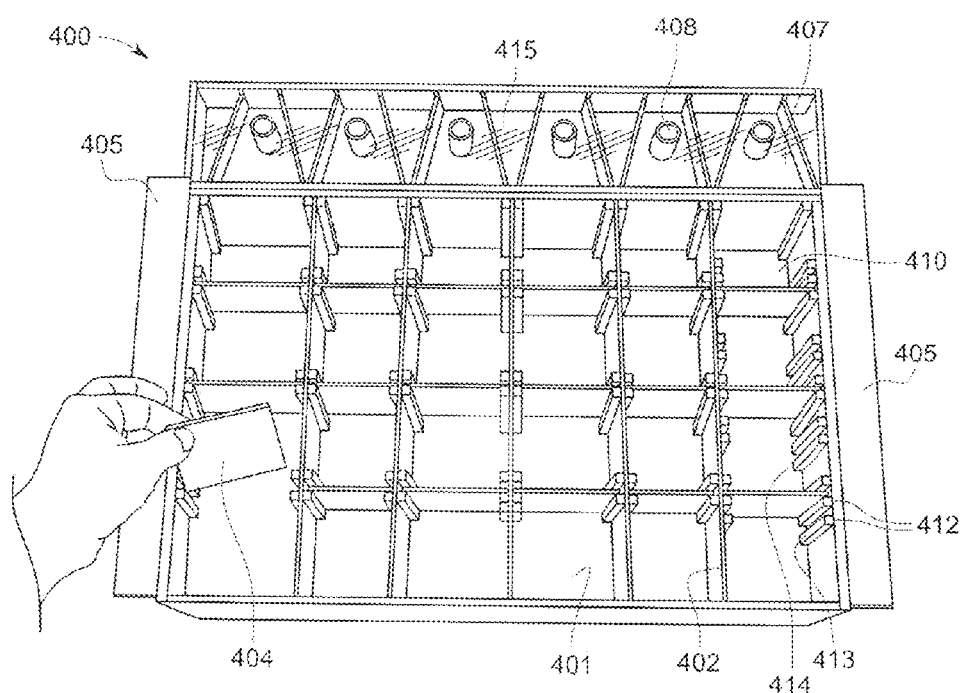
FIG. 24 is a perspective view of the tank of FIG. 18 illustrating the step of inserting/removing a sub-compartment divider in accordance with one embodiment of the present invention.
Figure 25:
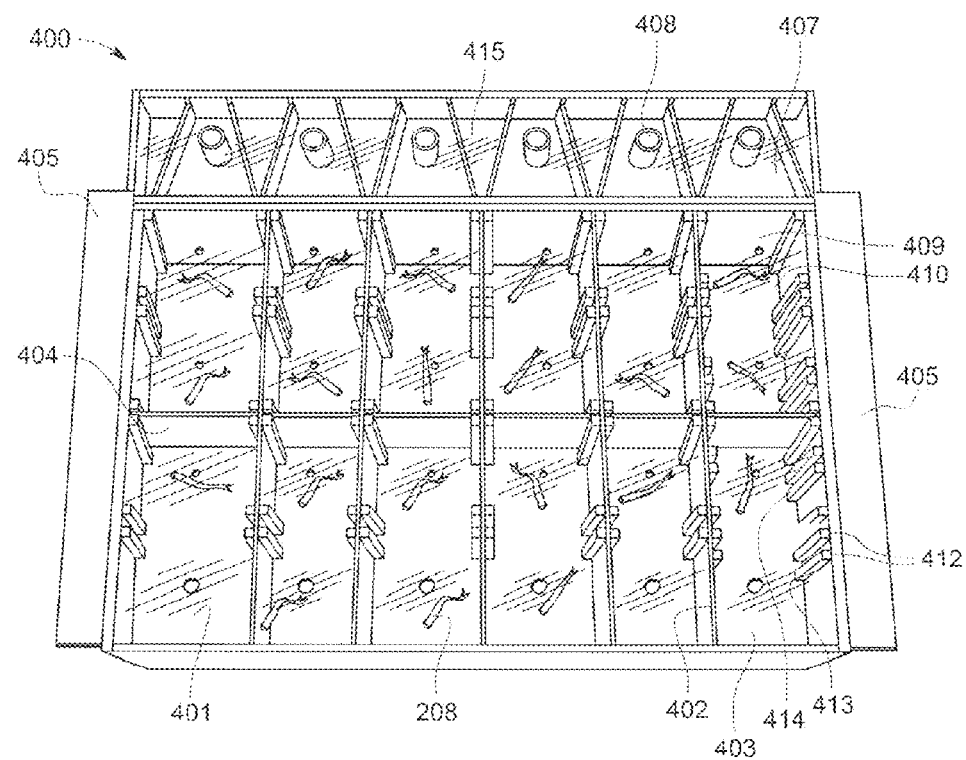
FIG. 25 is a top plan view of a tank divided into twelve sub-compartments in accordance with one embodiment of the present invention.
Figure 26:
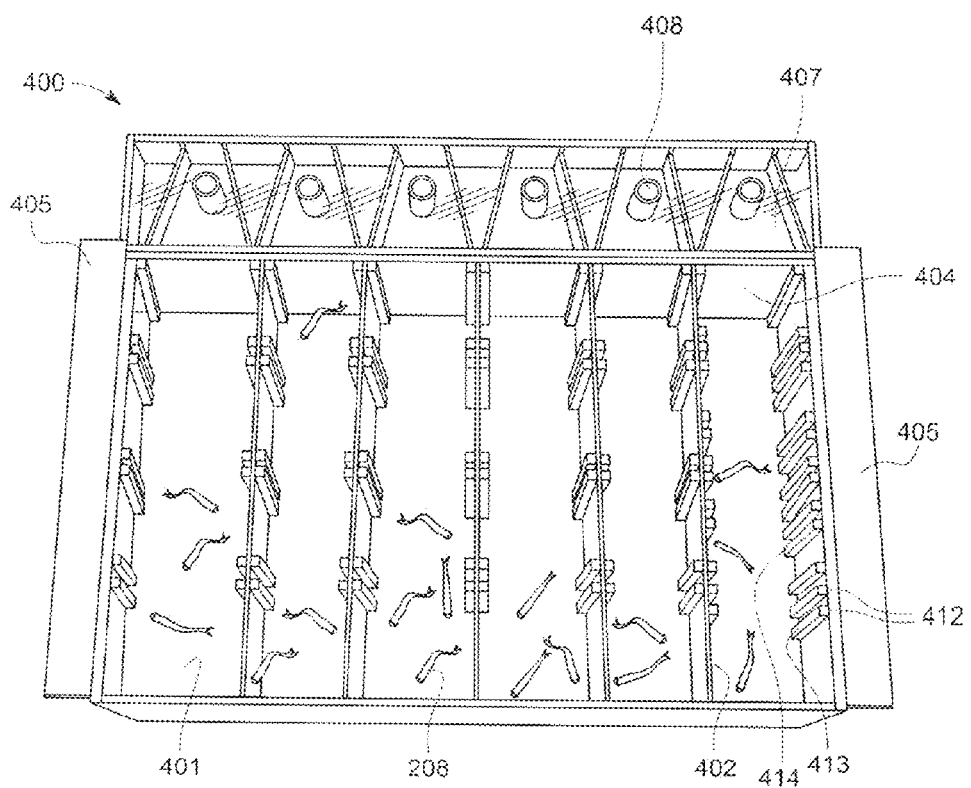
FIG. 26 is a top plan view of a tank filled with water and fish but without any sub-compartment dividers in accordance with one embodiment of the present invention.
Figure 27:
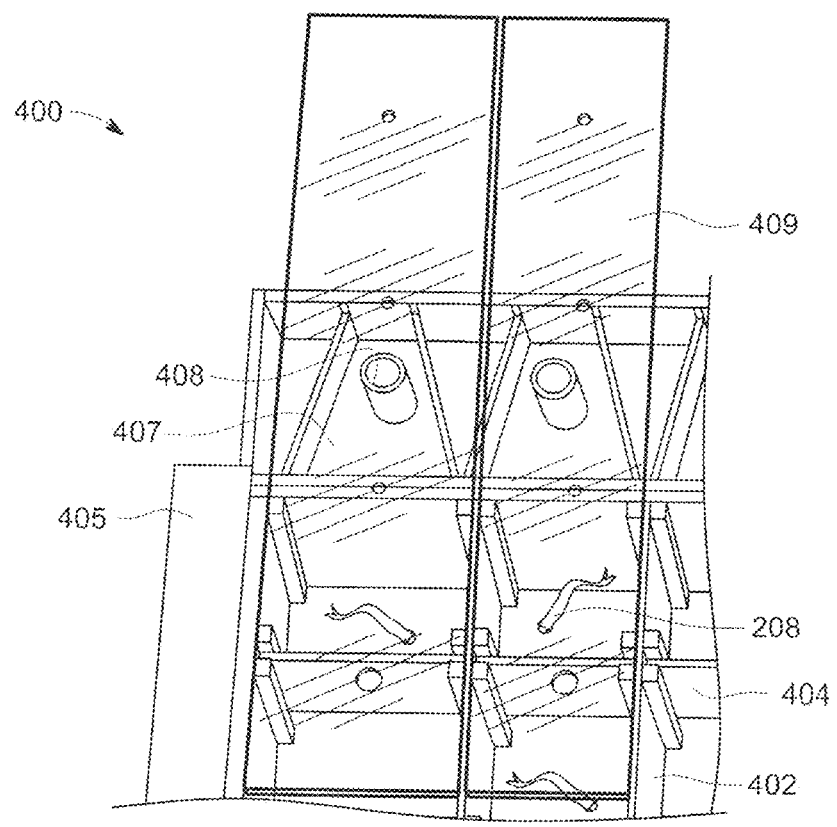
FIG. 27 is an expanded top plan view illustrating a sliding mechanism for inserting compartment lids in accordance with one embodiment of the present invention.
Figure 28A:
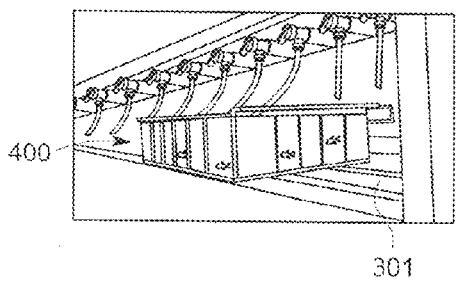
FIGS. 28A, 28B, 28C, and 28D illustrate front and perspective views of a tank on a housing rack, in accordance with one embodiment of the present invention.
Figure 28B:
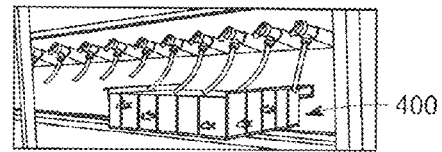
Figure 28C:
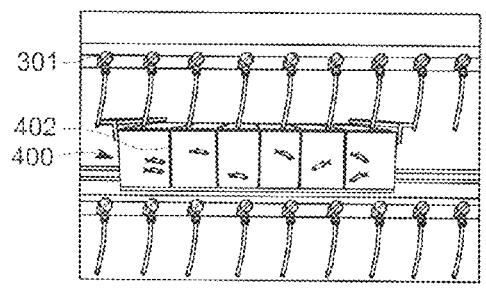
Figure 28D:
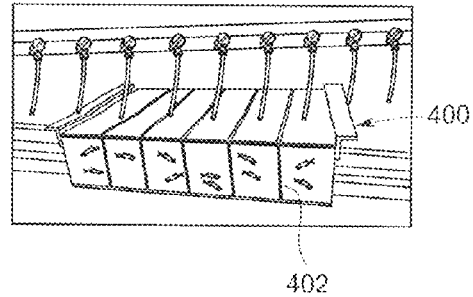

In FIG. 21, the compartment dividers 402 and the sub-compartment dividers are installed in such a manner that allows each compartment of the tank 400 to accommodate 24 fishes. FIG. 22 illustrates a water flow diagram showing a drainage trough 416 and a water supply hose 417 in the tank 400. Further, a gap 411 is illustrated (in FIGS. 22 and 23) in the sub-compartment divers 404 of the tank 400 for allowing food, water, and waste to pass to other compartments of the tank 400. A fish 208 is illustrated in the FIG. 23. FIG. 24 illustrates removal of the sub-compartment dividers 404 from the tank 400. FIG. 25 illustrates the tank 400 holding 12 pairs of fishes, such as fish 208. FIG. 26 illustrates a single sub-compartment divider 404 that is placed to prevent the fishes from escaping, wherein all other sub-compartment dividers are removed. FIG. 27 illustrates a lid 409 covered over each compartment of the tank 400.

FIGS. 28A, 28B, 28C, and 28D illustrate front and perspective views of the tank 400 housed on a housing rack 301. In an embodiment, the housing rack 301 is a 0.8 L rack. The housing rack 301 also houses larger individual tanks in accordance with an existing system and method for testing zebrafish. These views offer a comparison of the system 300 in accordance with one embodiment of the present invention and the existing system. The tank may be designed to fit on preexisting rack systems built by multiple manufacturers. Guides or rails on the bottom of the tank fit around the support bars on existing rack systems to lock the tank in place (as shown in FIG. 29A).

Figure 29A:
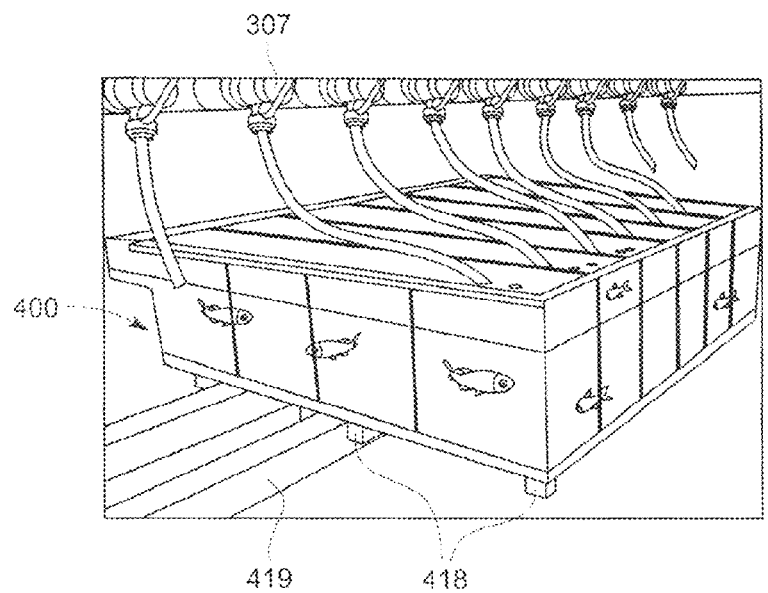
FIG. 29A illustrates a tank with rails at its bottom surface for locking the tank onto a tank-holding bar, in accordance with an embodiment of the present invention.
Figure 29B:
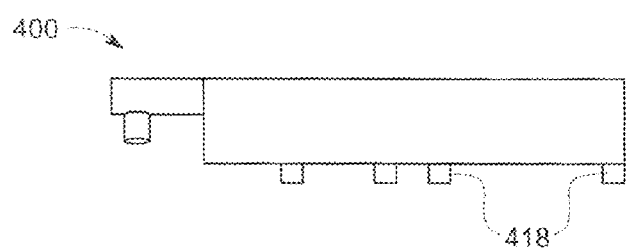
FIG. 29B illustrates side elevation view of the rails that is attached at the bottom surface of the tank for locking the tank onto the tank-holding bar.
Figure 29C:
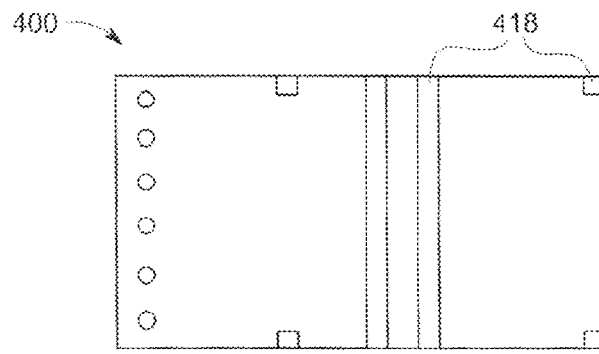
FIG. 29C illustrates bottom elevation view of the rails that is attached at the bottom surface of the tank for locking the tank onto the tank-holding bar.

FIG. 29A illustrates the tank 400 with rails 418 at its bottom surface. The rails 418 may be used for locking the tank 400 onto a tank-holding bar 419. Such additional feet (rails) 418 added to the bottom corners of the tank 400 stabilize the tank when the tank is on a flat surface. Further, side and bottom elevation views of the rails 418 are illustrated in FIGS. 29B and 29C, respectively.

Figure 30:
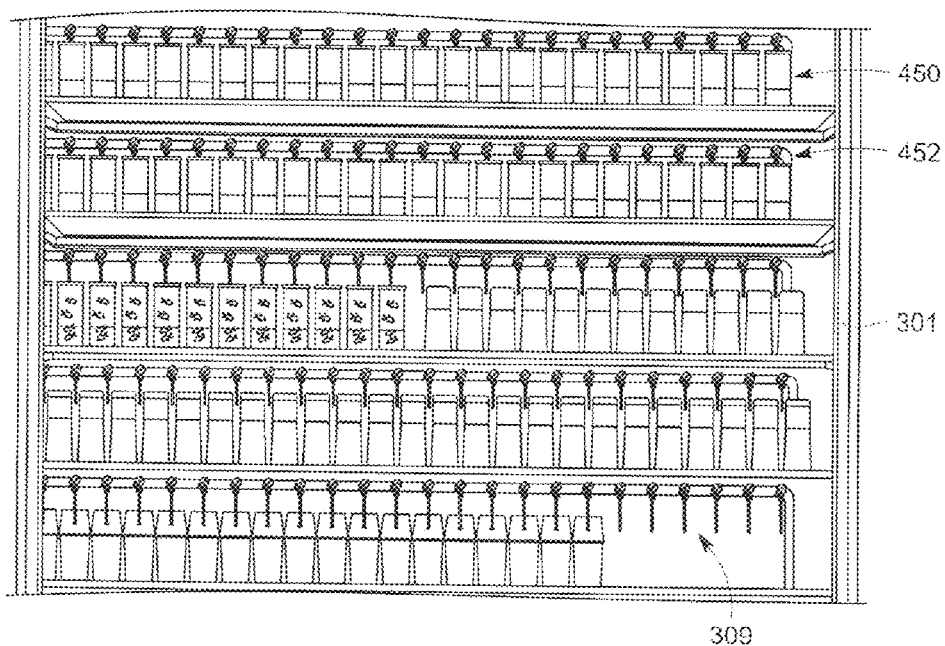
FIG. 30 is a front elevation view of a housing rack with larger individual tanks in accordance with an existing system and method for testing zebrafish.

FIG. 30 illustrates front elevation view of a housing rack 301 with larger individual tanks, such as tanks 450 for testing zebrafish. Further, in FIG. 30, a 1.8 L tank is shown. Furthermore various baffles 452 are also shown in the housing rack 301. Additionally a drainage trough 309 is illustrated in the housing rack 301.

Figure 31A:
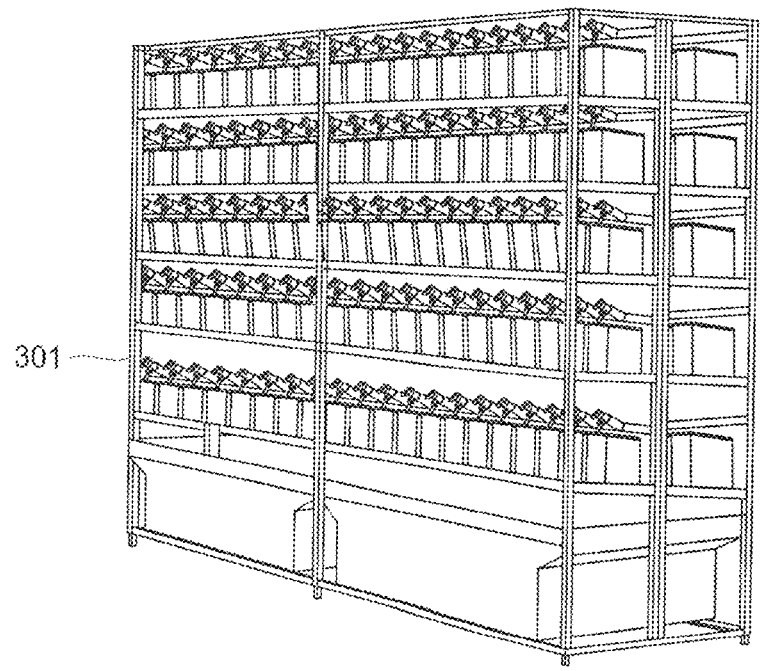
FIGS. 31A and 31B illustrate perspective view of a housing rack with larger individual tanks and a 96 well plate in accordance with an existing system and method for testing zebrafish.
Figure 31B:
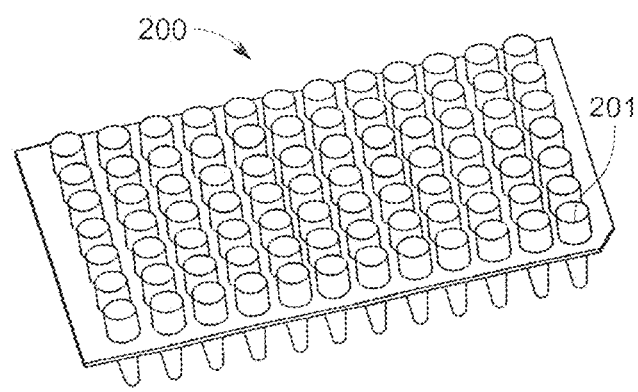

FIG. 31A illustrates a perspective view of a housing rack 301 with larger individual tanks for testing zebrafish. Further, FIG. 31B illustrates a 96 well plate 200 having 96 wells, such as a well 201.

Figure 32A:
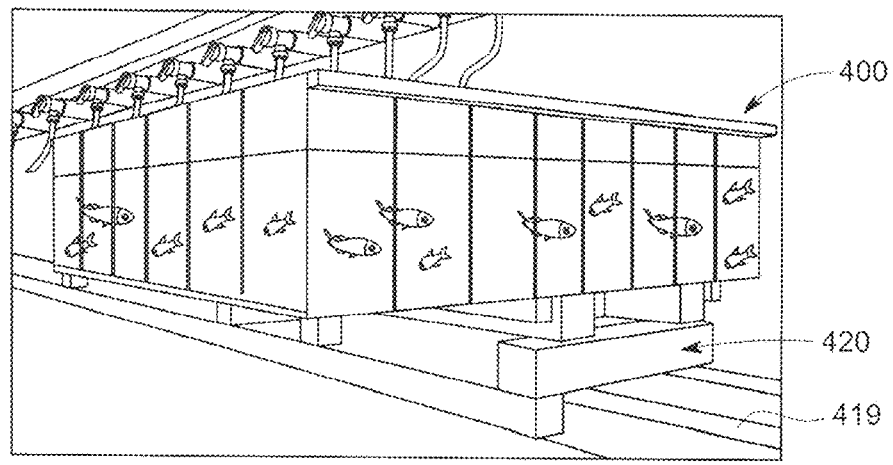
FIG. 32A illustrates a shelf adapter that allows the tank to fit on racks designed for taller tanks, in accordance with an embodiment of the present invention.

FIG. 32A illustrates a shelf adapter 420 that is used to accommodate a tank, such as tank 400, onto a housing rack that is designed to accommodate substantially taller tanks. Zebrafish research holding system manufacturers generally build two different types of shelves/housing racks. One is designed to hold short holding tanks and the other is designed to hold taller holding tanks. The system may accommodate the tank on shelves designed to hold short holding tanks with little or no modification. In case, if a tank is to be placed on a shelf designed to hold taller holding tanks, then the shelf adapter 420 is required to be used (as shown in FIG. 32A). Further, the shelf adapter 420 is designed to lock on the existing shelf/housing rack for locking the tank on the shelf adapter 420. The shelf adapter 420 also enables the tank drain spouts to fit into the drainage trough of a tall holding tank shelf.

Figure 32B:
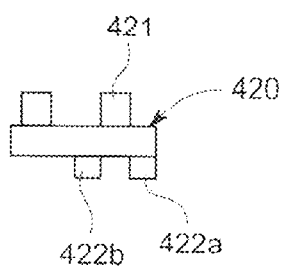
FIG. 32B illustrates side elevation view of the shelf adapter that allows the tank to fit on racks designed for taller tanks.
Figure 32C:
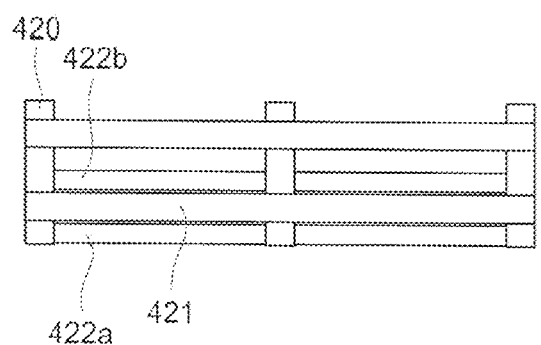
FIG. 32C illustrates top plan view of the shelf adapter that allows the tank to fit on racks designed for taller tanks.

Further, the shelf adapter 420 has rails that lock the shelf adapter 420 onto a rack system and a bar that allows the tank to lock on to the shelf adapter 420. Side view and bottom views of the shelf adapter are illustrated in FIGS. 32B and 32C respectively. In an exemplary embodiment, the dark shaded bars, such as bar 421, may be of dimension 1", and the light shaded bars, such as bars 422a and 422b, may be of dimension ¾'. Additionally, as shown in the FIG. 32B, the gap between the two light shaded bars (i.e. 422a and 422b) is in-line with the dark shaded bar 421 above. Furthermore, the dimensions shown in the FIGS. 32B and 32C are meant only for enabling a person skilled in the art to implement the present invention. However, the dimensions are not mean for restricting the scope of the present invention.

Figure 33:
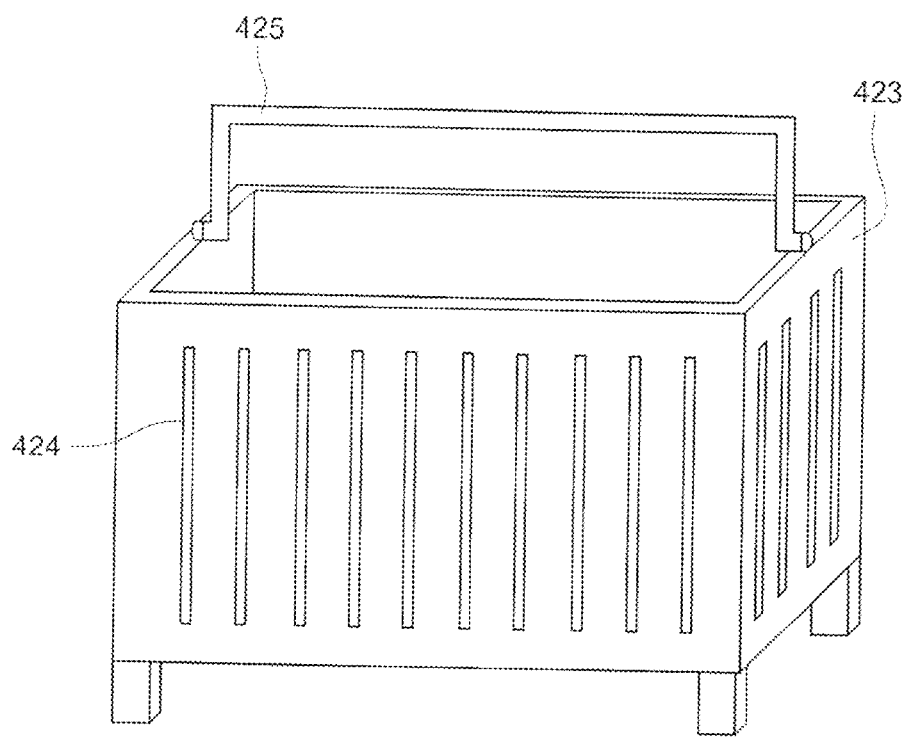
FIG. 33 illustrates a basket that may be placed into the tank for allowing easier removal of aquatic species from each compartment of the tank.

FIG. 33 illustrates a basket 423 that may be placed into a tank, such as tank 400, for facilitating removal of aquatic species, such as zebrafish, from the tank 400. In an embodiment of the present invention, the basket 423 is removable. Further, for easier removal of the aquatic species from the tank 400, baskets 423 containing slots/holes 424 may be placed into each compartment of the tank 400. Such basket 423 facilitates easier removal of the aquatic species from each compartment of the tank 400. This eliminates the need to net each aquatic species out of the compartments of the tank 400. Further, the baskets 423 may or may not be used in conjunction with section dividers. Additionally, each basket 423 has a handle 425 for easy removal of the basket 423 from the compartments of the tank 400. The handle 425 may be folded (not shown) into edge of the basket 423.

Figure 34:
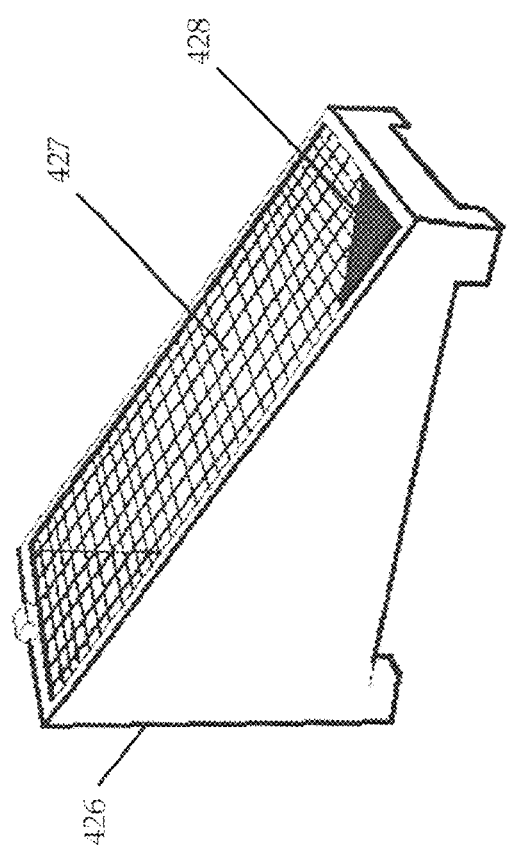
FIG. 34 illustrates a 'spawning insert' that may be placed into the tank for facilitating spawning process of aquatic species.

FIG. 34 illustrates a 'spawning insert' 426 that may be placed into a tank, such as tank 400, for facilitating spawning process of aquatic species, such as a fish/zebrafish. By using the spawning insert 426, fishes may be spawned directly in the tank 400. This eliminates the need for a separate spawning vessel. Further, to make use of the spawning inserts 426, the spawning inserts 426 are placed inside each compartment of the tank 400 and then fishes are added into the compartments containing spawning inserts 426. Further, the sloped and rough spawning surface of the spawning insert 426 helps in initiating spawning. When a fish spawn, eggs of the fish get sink through a large screen 427 covering the top of the spawning insert 426 and come to rest on a fine mesh screen 428 at the bottom of the spawning insert 426.

After a set amount of time, usually a night, the spawning/breeding inserts 426 are removed and the eggs are collected into Petri dishes (not shown) or the like which are labeled with the coordinates of the location of the breeding pair in the tank. As the eggs are removed, the fish is not required to be removed from the tank 400. Embryos of eggs are then screened for phenotype, genotype, or transgenic expression, and fish from clutches of interest are easily located in the tank.

Figure 35:
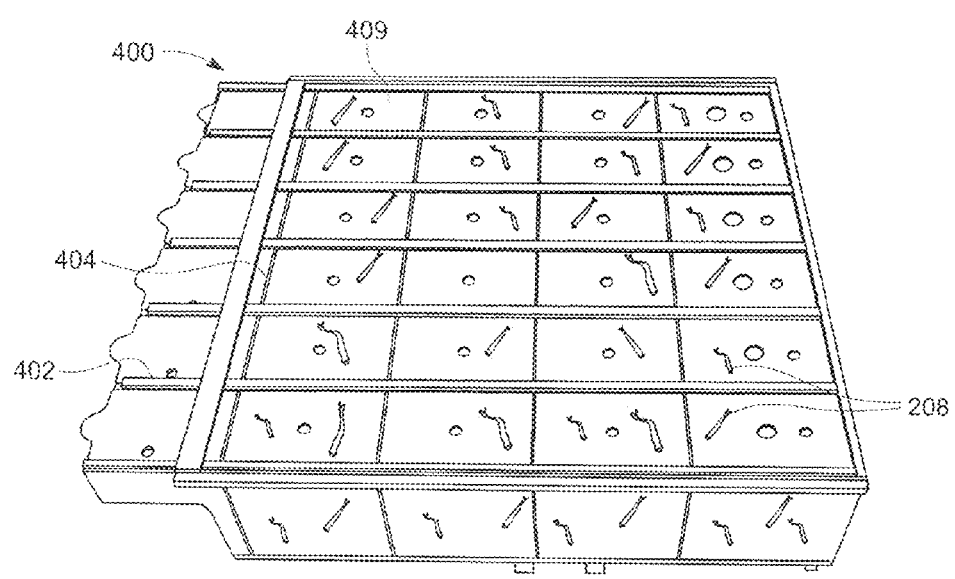
FIG. 35 is a tank fabricated out of acrylic with lids and dividers fabricated out of polycarbonate.

FIG. 35 illustrates an exemplary embodiment of the present invention wherein a tank is fabricated out of acrylic and its dividers and lids are fabricated out of polycarbonate.

Figure 36:
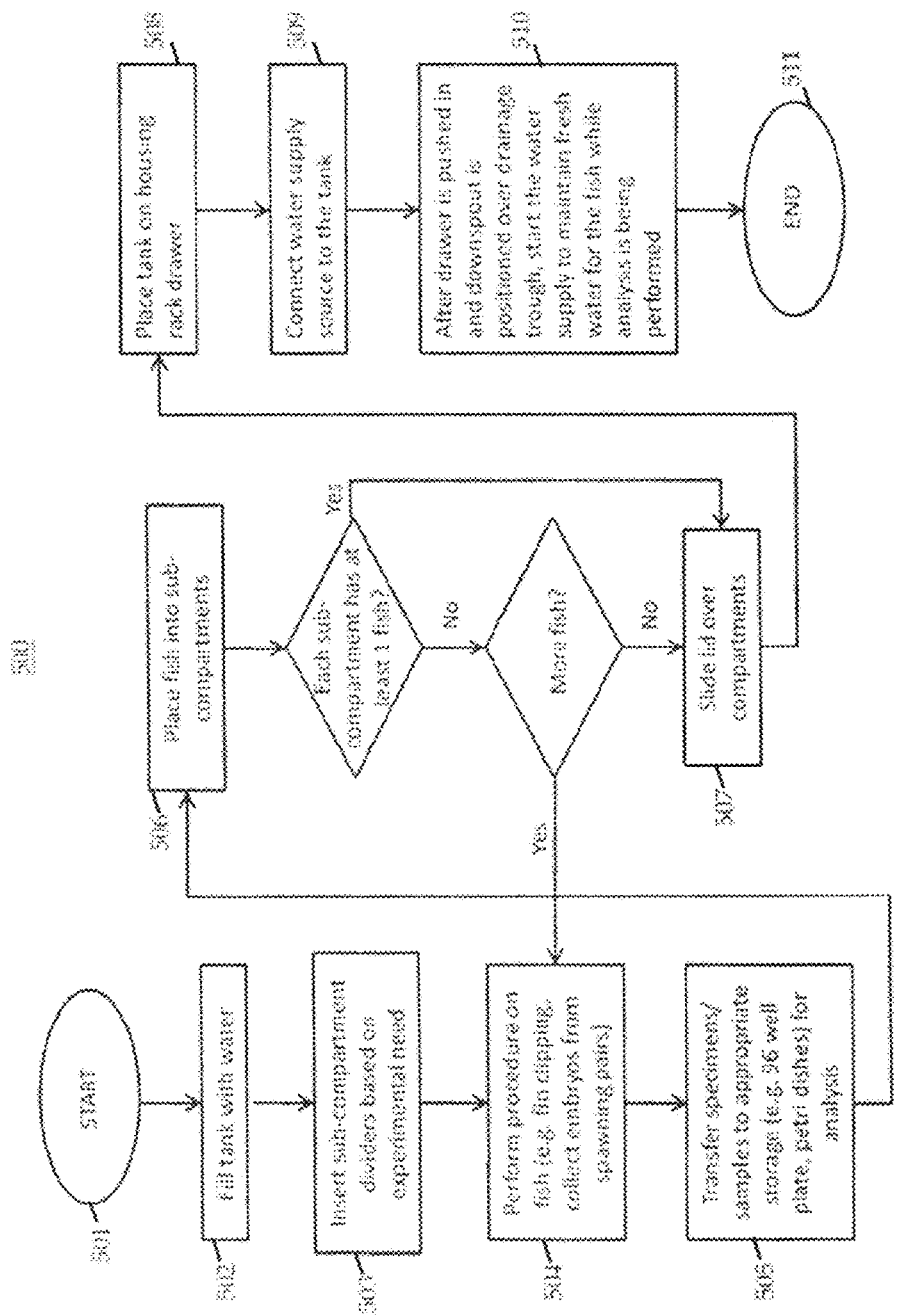
FIG. 36 is a flowchart illustrating an exemplary method in accordance with one embodiment of the present invention.

FIG. 36 is a flowchart illustrating an exemplary method 500 for testing and researching fish in accordance with one embodiment of the present invention. The method 500 begins at step 501. At step 502, the researcher fills a tank with water. The tank may be as depicted in FIG. 1 or 17, or any other variation thereof. At step 503, the researcher inserts the required number of sub-compartment dividers to create the necessary number of sub-compartments given the type of testing to be performed. For example, if embryonic screening for mutant phenotypes is being performed, less sub-compartment dividers will be required as the fish will be housed in pairs in each sub-compartment. At step 504, the researcher performs the procedure on the fish, for example collecting embryos from spawning pairs. At step 505, the researcher transfers the samples taken in step 504 to the appropriate storage device, such as a petri dish, beaker, test tube, 96 well plate, and the like, given the specific type of testing and research being performed. At step 506, the researcher places the fish into the sub-compartments of the tank. If there are any empty sub-compartments and additional fish are to be tested, then the researcher repeats steps 504 through 506 until all the sub-compartments are filled. Otherwise, the researcher will proceed to step 507. At step 507, the researcher slides a compartment lid over each compartment. At step 508, the researcher transfers the tank to the housing rack by placing the tank on the drawer. At step 509, the researcher connects the water supply source to each compartment and pushes the drawer in such that each of the downspouts are positioned over the drainage trough located on each housing rank shelf. At 510, the researcher starts the water supply to each compartment so that fresh water can constantly circulate from each sub-compartment to the next to the collection channel and downspout. The method ends at step 511.

While the foregoing is directed to embodiments of the present invention, other and further embodiments of the present invention may be devised without departing from the basic scope thereof. In particular, it should be appreciated that any element of any embodiments disclosed herein may be combined with any other elements from any other embodiments disclosed herein, in accordance with yet further embodiments of the present invention.

The present invention, in various embodiments, configurations, and aspects, includes components, methods, processes, systems and apparatus substantially as depicted and described herein, including various embodiments, sub-combinations, and subsets thereof. Those of skill in the art will understand how to make and use the present invention after understanding the present disclosure. The present invention, in various embodiments, configurations, and aspects, includes providing apparatus and processes in the absence of items not depicted and/or described herein or in various embodiments, configurations, or aspects hereof, including in the absence of such items as may have been used in previous devices or processes, e.g., for improving performance, achieving ease and reducing cost of implementation.

The foregoing discussion of the present invention has been presented for purposes of illustration and description. The foregoing is not intended to limit the present invention to the form or forms disclosed herein. In the foregoing Detailed Description for example, various features of the present invention are grouped together in one or more embodiments, configurations, or aspects for the purpose of streamlining the disclosure. The features of the embodiments, configurations, or aspects of the present invention may be combined in alternate embodiments, configurations, or aspects other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment, configuration, or aspect. Thus, the following claims are hereby incorporated into this detailed description, with each claim standing on its own as a separate preferred embodiment of the present invention.

Moreover, though the description of the present invention has included description of one or more embodiments, configurations, materials, measurements, dimensions, or aspects and certain variations and modifications, other variations, combinations, and modifications are within the scope of the present invention, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for testing and researching aquatic species, the system comprising:
   a housing rack;
   at least one tank sized to be received by the housing rack, wherein the at least one tank comprises at least one compartment having at least one divider;
   a drain for draining water from the at least one compartment; and
   at least one removable basket in the at least one compartment for allowing removal of aquatic species from the at least one tank.

2. The system of claim 1, wherein the at least one tank further comprises a spawning insert for spawning the aquatic species.

3. The system of claim 1, wherein the at least one tank further comprises sub-compartments within the at least one compartment.

4. The system of claim 1, wherein the at least one divider further comprises a gap for allowing water, food, and waste to flow from the at least one compartment to another compartment.

5. The system of claim 1, wherein the at least one divider further comprises at least one opening for allowing water to flow from the at least one compartment to another compartment.

6. An apparatus for testing and researching aquatic species, comprising:
   at least one tank;
   a drain for draining water from the at least one tank; and
   at least one removable basket in the at least one tank for allowing removal of aquatic species from the at least one tank,
   wherein the at least one tank further comprises a spawning insert for spawning the aquatic species.

7. The apparatus of claim 6, wherein the at least one tank comprises at least one compartment.

8. The apparatus of claim 7, wherein the at least one compartment comprises at least one divider.

9. The apparatus of claim 8 wherein the at least one divider further comprises a gap for allowing water, food, and waste to flow from the at least one compartment to another compartment.

10. The apparatus of claim 8, wherein the at least one divider further comprises at least one opening for allowing water to flow from the at least one compartment to another compartment.

11. The apparatus of claim 8, wherein the at least one divider further comprises an opening covered by a mesh.

12. The apparatus of claim 7, wherein the at least one tank further comprises sub-compartments within the at least one compartment.

13. A system for testing and researching aquatic species, the system comprising:
- at least one tank comprising at least one compartment, said compartment having at least one divider;
- a drain for each at least one compartment for draining water from the at least one compartment;
- at least one removable basket in the at least one compartment for allowing removal of aquatic species from the at least one tank;
- a housing rack;
- at least one drawer housed within the housing rack;
- a water collection tank into which water from the at least one drainage trough drains; and
- a pump for pumping the water from the water collection tank.

14. The system of claim 13, wherein the at least one tank further comprises a spawning insert for spawning the aquatic species.

15. The system of claim 13, wherein the at least one tank further comprises sub-compartments within the at least one compartment.

16. The system of claim 13 wherein the at least one divider further comprises a gap for allowing water, food, and waste to flow from the at least one compartment to another compartment.

17. The system of claim 13, wherein the at least one divider further comprises at least one opening for allowing water to flow from the at least one compartment to another compartment.

18. The system of claim 13, wherein the at least one divider further comprises an opening covered by a mesh.

19. The system of claim 13, wherein the at least one removable basket comprises at least one slot, at least one hole, and at least one handle.

* * * * *